United States Patent [19]

Takemura et al.

[11] Patent Number: 5,654,318

[45] Date of Patent: Aug. 5, 1997

[54] BICYCLIC AMINE DERIVATIVES

[75] Inventors: Makoto Takemura; Youichi Kimura; Norikazu Matsuhashi, all of Tokyo, Japan

[73] Assignee: Daiichi Pharmaceutical Co., Ltd., Tokyo, Japan

[21] Appl. No.: 172,233

[22] Filed: Dec. 23, 1993

[30] Foreign Application Priority Data

Dec. 25, 1992 [JP] Japan ................... 4-346030

[51] Int. Cl.$^6$ .............. A61K 31/47; C07D 215/12; C07D 215/56; C07D 209/02
[52] U.S. Cl. .............. 514/314; 546/156; 546/158; 546/168; 548/455
[58] Field of Search .................. 546/162, 156, 546/158, 168; 548/454, 455; 514/314

[56] References Cited

FOREIGN PATENT DOCUMENTS

| 0191185 | 12/1985 | European Pat. Off. |
| 0341493 | 4/1989 | European Pat. Off. |
| 0350733 | 6/1989 | European Pat. Off. |
| 0424850 | 10/1989 | European Pat. Off. |
| 0391132 | 3/1990 | European Pat. Off. |
| 0429304 | 11/1990 | European Pat. Off. |
| 0481274 | 9/1991 | European Pat. Off. |
| 0550903 | 12/1992 | European Pat. Off. |
| 3188080 | 8/1991 | Japan. |
| 9221659 | 12/1992 | Japan. |

OTHER PUBLICATIONS

CA 113: 97462, (Petersen DE 3906363) Jan. 18 1990.
Shohgo Atarashi et al., "Fluorocyclopropyl Quinolones. 1. Synthesis and Structure–Activity...", Journal of Medicinal Chemistry, vol. 36, No. 22, 1993, pp. 3444–3448.
Bremm et al., "In vitro Evaluation of BAY Y3118, a New Full–Spectrum Fluoroquinolone", Chemotherapy vol, 38, No. 6, 1992, pp. 376–387.

*Primary Examiner*—Shean G. Wu
*Attorney, Agent, or Firm*—Sughrue, Mion, Zinn, Macpeak & Seas

[57] ABSTRACT

A compound represented by formula (I) or a salt thereof:

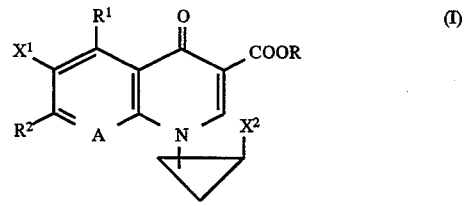

wherein $X^1$ and $X^2$ each represent a halogen atom;

$R^1$ represents a hydrogen atom or a substituent;

$R^2$ represents a substituted or unsubstituted bicyclic heterocyclic substituent of the following formula;

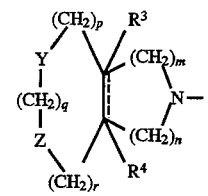

wherein $R^3$, $R^4$, Y, Z, m, n, p, q and r are as defined herein;

A represents a nitrogen atom or a substituted carbon atom; and

R represents a hydrogen atom or a substituent. The compound exhibits potent antimicrobial activity and also high safety due to reduced lipophilicity.

14 Claims, No Drawings

BICYCLIC AMINE DERIVATIVES

FIELD OF THE INVENTION

This invention relates to an antimicrobial compound useful as a medicament for humans, animals, and fishes and an antimicrobial preservative, and an antimicrobial agent containing the same.

BACKGROUND OF THE INVENTION

Quinolone derivatives are known as synthetic antimicrobial agents having a fused pyridonecarboxylic acid skeleton. It is known that those having a cyclopropyl group at the 1-position exhibit potent antimicrobial activity. Further, quinolone derivatives having a fluorine atom introduced into the 2-position of the cyclopropyl group in a cis-configuration with respect to the fused pyridonecarboxylic acid moiety also exhibit potent antimicrobial activity. These quinolone derivatives are considered to have not only high antimicrobial activity but high safety (see EP-A-0191185 and EP-A-0341493).

Besides antimicrobial activity, in vivo behavior of quinolone derivatives is of importance for safety and efficacy. In vivo behavior of quinolone derivatives, such as oral absorbability, distribution, and excretion, is greatly related to lipophilicity and water-solubility of quinolone molecules. The antimicrobial activity of quinolone derivatives is largely influenced by the structure of a cyclic amine substituent on the 7-position (or a position corresponding to the 7-position) of the quinoline skeleton. However, quinolone compounds with a cyclic amine substituent which have been experimentally verified to exhibit potent antimicrobial activity often fail to clinically show their superiority. The present inventors considered that one of the reasons of such a phenomenon consists in lipophilicity of quinolone molecules and found that quinolone derivatives having a halogenocyclopropyl group, especially a fluorocyclopropyl group, at the 1-position (or a position corresponding to the 1-position) thereof have well-balanced lipophilicity and thereby exhibit high safety and high efficacy as well as excellent antimicrobial activity.

On the other hand, quinolone derivatives having a cis-halogenocyclopropyl group at the 1-position possess excellent properties in terms of antimicrobial activity and safety. These quinolone derivatives contain a pair of enantiomers due to the halogenocyclopropane ring moiety regardless of stereoisomerism at the other position, which is ascribed to the stereochemical relationship between the pyridonecarboxylic acid moiety and the halogen atom on the cyclopropane ring. It is possible to apply a racemic compound of the quinolone derivative, a mixture of enantiomers, as a medicament as such.

Where stereoisomerism exists at a position other than the halogenocyclopropane moiety, particularly at the 7-positioned substituent, such quinolone derivatives contain diastereomers, that is, at least 4 kinds of stereoisomers. A mixture of diastereomers is a mixture of isomers having different physical properties and is difficult to apply as a medicament as such.

SUMMARY OF THE INVENTION

The present inventors have conducted extensive investigations for the purpose of obtaining a 1-(1,2-cis-2-fluorocyclopropyl)-substituted quinolone derivative which consists of a single stereoisomer even if it may contain diastereomers.

As a result, the inventors have succeeded in separately obtaining each stereoisomer of cis-2-fluorocyclopropylamine as a pure isomer. Starting with this cis-fluorocyclopropylamine, the inventors separately obtained each antipode of a quinolone derivative attributed only to the steric configuration of the fluorocyclopropane ring thereof.

Now that the above-mentioned quinolone derivative useful as an intermediate has been obtained, it is possible to synthesize an optically active quinolone derivative consisting solely of a single diastereomer by reacting the intermediate quinolone derivative with a nitrogen-containing heterocyclic compound consisting solely of a single isomer at introducing a nitrogen-containing heterocyclic substituent into the 7-position of the former.

The inventors have ascertained that each of the resulting diastereomers exhibits potent antimicrobial activity and also has high safety with markedly improved selective toxicity and thus completed the invention.

The present invention relates to a compound represented by formula (I):

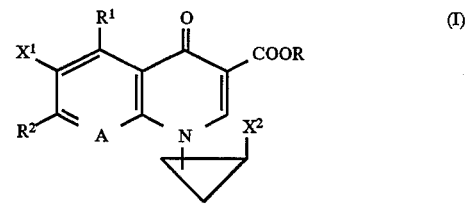

wherein $X^1$ and $X^2$, which may be the same or different, each represents a halogen atom;

$R^1$ represents a hydrogen atom, a hydroxyl group, a thiol group, a halogenomethyl group, an alkyl group having from 1 to 6 carbon atoms, an alkoxy group having from 1 to 6 carbon atoms or a substituted or unsubstituted amino group;

$R^2$ represents a bicyclic heterocyclic substituent represented by formula:

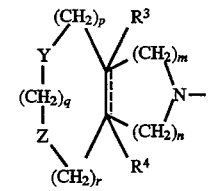

wherein $R^3$ and $R^4$, which may be the same or different, each represents a hydrogen atom, an alkyl group having from 1 to 4 carbon atoms or an alkoxy group having from 1 to 4 carbon atoms; or $R^3$ and $R^4$ may be taken together to form a single bond, providing a double bond between the two carbon atoms to which they are bonded;

Y represents an oxygen atom, a sulfur atom, a group of formula:

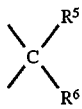

wherein $R^5$ and $R^6$ which may be the same or different, each represents a hydrogen atom or an alkyl group having from 1 to 6 carbon atoms, a group of formula:

wherein $R^7$ represents a hydrogen atom, a formyl group, an acyl group having from 2 to 5 carbon atoms or an alkyl group having from 1 to 4 carbon atoms, a group of formula:

wherein $R^8$ represents a hydrogen atom, a formyl group, an acyl group having from 2 to 5 carbon atoms or an alkyl group having from 1 to 4 carbon atoms, or a group of formula:

wherein $R^9$ represents a hydrogen atom, a formyl group, an acyl group having from 2 to 5 carbon atoms or an alkyl group having from 1 to 4 carbon atoms;

Z represents an oxygen atom, a sulfur atom, a group of formula:

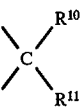

wherein $R^{10}$ and $R^{11}$, which may be the same or different, each represents a hydrogen atom or an alkyl group having from 1 to 6 carbon atoms, a group of formula:

wherein $R^{12}$ represents a hydrogen atom, a formyl group, an acyl group having from 2 to 5 carbon atoms or an alkyl group having from 1 to 4 carbon atoms, a group of formula:

wherein $R^{13}$ represents a hydrogen atom, a formyl group, an acyl group having from 2 to 5 carbon atoms or an alkyl group having from 1 to 4 carbon atoms, or a group of formula:

wherein $R^{14}$ represents a hydrogen atom, a formyl group, an acyl group having from 2 to 5 carbon atoms or an alkyl group having from 1 to 4 carbon atoms, m and n each independently represents an integer of from 0 to 2, with the sum of m and n being an integer of 2 or 3; and p, q, and r each independently represents an integer of from 0 to 3, with the sum of p, q, and r being an integer of from 0 to 3, said bicyclic heterocyclic substituent may be substituted with 1 to 4 alkyl groups each having from 1 to 6 carbon atoms;

A represents a nitrogen atom or a group of formula:

wherein $X^3$ represents a hydrogen atom, a halogen atom, a cyano group, a trifluoromethyl group, an alkyl group having from 1 to 6 carbon atoms, an alkoxy group having from 1 to 6 carbon atoms or a substituted or unsubstituted amino group; and R represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having from 1 to 6 carbon atoms, an alkyloxymethyl group having from 2 to 7 carbon atoms or a phenylalkyl group composed of an alkylene moiety having from 1 to 6 carbon atoms and a phenyl moiety, or a salt thereof.

The present invention relates to a compound of formula (I) wherein $R^2$ is a heterocyclic substituent having a single stereoisomerism or a salt thereof.

The present invention relates to a compound of formula (I) wherein the 1,2-cis-halogenocyclopropyl group is a substituent having a single stereoisomerism or a salt thereof.

The present invention relates to a compound of formula (I) wherein the 1,2-cis-halogenocyclopropyl group is a (1R, 2S)-2-halogenocyclopropyl group or a salt thereof.

The present invention relates to a compound of formula (I) wherein $X^2$ is a fluorine atom or a salt thereof.

The present invention relates to a compound of formula (I) wherein $R^2$ is a substituent selected from a group consisting of a 2,8-diazabicyclo[4.3.0]nonan-8-yl group, a 3,7-diazabicyclo[3.3.0]oct-1(5)-ene-3-yl group and 2-oxa-5,8-diazabicyclo[4.3.0]nonan-8-yl group.

The present invention relates to a compound of formula (I) wherein the compound consists of a single diastereomer, or a salt thereof.

The present invention relates to a compound selected from a group consisting of 8-chloro-7-(2,8-diazabicyclo [4.3.0]nonan-8-yl)-8-chloro-6-fluoro-1-[(1R,2S) -2-fluorocyclopropyl]-1,4-dihydro-4-oxoquinoline-3-carboxylic acid, 5-amino-7-[(S,S)-2,8-diazabicyclo[4.3.0] nonan-8-yl]-6,8-difluoro-1-[(1R,2S)-2-fluorocyclopropyl]-1,4-dihydro-4 -oxoquinoline-3-carboxylic acid, 7-[(S,S)-2, 8-diazabicyclo[4.3.0]nonan-8-yl]-6-fluoro-1-[(1R,2S)-2-fluorocyclopropyl]-8-methyl-1,4-dihydro-4-oxoquinoline-3-carboxylic acid, 7-[(S,S)-2,8-diazabicyclo[4.3.0]nonan-8-yl]-6,8-difluoro-1-[(1R,2S)-2-fluorocyclopropyl]-1,4-dihydro-4-oxoquinoline-3-carboxylic acid, 8-chloro-7-[3,7-diazabicyclo[3.3.0]oct-1(5)-ene-3-yl]-6-fluoro-1-[(1R,2S)-2-fluorocyclopropyl]-1,4-dihydro-4-oxoquinoline-3-carboxylic acid, (+)-8-chloro-6-fluoro-1-[(1R,2S)-2-fluorocyclopropyl]-7-[trans-2-oxa-5,8-diazabicyclo[4.3.0] nonan-8-yl]-1,4-dihydro-4-oxoquinoline-3-carboxylic acid, (−)-8-chloro-6-fluoro-1-[(1R,2S)-2-fluorocyclopropyl]-7-[trans-2-oxa-5,8-diazabicyclo[4.3.0]nonan-8-yl]-1,4-dihydro-4-oxoquinoline-3-carboxylic acid, 5-amino-6,8-difluoro-1-[(1R,2S)-2-fluorocyclopropyl]-7-(trans-2-oxa-5, 8-diazabicyclo[4.3.0]nonan-8-yl)-1,4-dihydro-4-oxoquinoline-3-carboxylic acid, (−)-5-amino-7-[cis-2-azabicyclo[4.3.0]nonan -8-yl]-6,8-difluoro-1-[(1R,2S)-2-fluorocyclopropyl]-1,4-dihydro-4-oxoquinoline-3-carboxylic acid, and 8-chloro-6-fluoro-1-[(1R,2S)-2-fluorocyclopropyl]-7-(cis-2-oxa-5,8-diazabicyclo[4.3.0] nonan-8-yl)-1,4-dihydro-4-oxoquinoline-3-carboxylic acid, or a salt thereof.

The present invention relates to an antimicrobial agent containing the above-mentioned compound as an active ingredient.

DETAILED DESCRIPTION OF THE INVENTION

Detailed explanation on the compounds of the present invention is described below. At first, an explanation for the substituents is described.

As to the substituent $X^1$, $X^2$ and $X^3$, in case when these are halogen atoms, $X^1$ and $X^3$ are preferably fluorine atoms, and $X^2$ is preferably a fluorine atom or a chlorine atom, more preferably a fluorine atom.

$R^1$ is a hydrogen atom, a hydroxyl group, a thiol group, a halogenomethyl group, an alkyl group having from 1 to 6 carbon atoms, an alkoxy group having from 1 to 6 carbon atoms or a substituted or unsubstituted amino group. The alkyl group as represented by $R^1$ may be straight or branched alkyl group having from 1 to 6 carbon atoms and preferably includes a methyl group, an ethyl group, an n-propyl group, and an isopropyl group. Fluorine atom is a preferable species for the halogenoalkyl group, and the halogenoalkyl group preferably includes from 1 to 3 fluorine atoms. The halogenomethyl group as $R^1$ preferably includes from 1 up to 3 fluorine atoms. Preferable examples of the halogenomethyl groups include a fluoromethyl group and a difluoromethyl group. Substituents which may be on the amino group as $R^1$ include a formyl group, an alkyl group having from 1 to 6 carbon atoms, and an acyl group having from 2 to 5 carbon atoms. In the case of an alkyl-substituted amino group, the amino group may have two alkyl groups.

The amino group, hydroxyl group or thiol group as $R^1$ may be protected with a commonly employed protective group, such as an alkoxycarbonyl group, e.g., a t-butoxycarbonyl group and a 2,2,2-trichloroethoxycarbonyl group; an aralkyloxycarbonyl group, e.g., a benzyloxycarbonyl group, a p-methoxybenzyloxycarbonyl group, and a p-nitrobenzyloxycarbonyl group; an acyl group, e.g., an acetyl group, a methoxyacetyl group, a trifluoroacetyl group, a chloroacetyl group, a pivaloyl group, a formyl group, and a benzoyl group; an alkyl group or an aralkyl group, e.g., a t-butyl group, a benzyl group, a p-nitrobenzyl group, a p-methoxybenzyl group, and a triphenylmethyl group; an ether group, e.g., a methoxymethyl group, a t-butoxymethyl group, a tetrahydropyranyl group, and a 2,2,2-trichloroethoxymethyl group; and a silyl group, e.g., a trimethylsilyl group, an isopropyldimethylsilyl group, a t-butyldimethylsilyl group, a tribenzylsilyl group, and a t-butyldiphenylsilyl group.

The substituent $R^2$ is a bicyclic nitrogen-containing heterocyclic substituent. The nitrogen-containing heterocyclic substituent is a substituent derived from a nitrogen-containing heterocyclic compound. Preferable heterocyclic substituents are saturated ones, and in other words, a substituent derived from an alicyclic compound with its carbon atom constituting the cyclic structure thereof being replaced with a nitrogen atom.

A preferable ring system of the bicyclic substituents are a bicyclo[3.3.0], [4.3.0], [5.3.0], [4.4.0] or [5.4.0] system. One of the two rings is a 5- or 6-membered ring containing one nitrogen atom, via which the heterocyclic substituent $R^2$ is usually bonded to the 7-position of the quinoline ring or naphthylidine ring. This nitrogen-containing ring is fused with a second 4- to 7-membered ring which may contain one or more hetero atoms selected from a group consisting of a nitrogen atom, an oxygen atom, and a sulfur atom. Where the second ring contains a nitrogen atom, the nitrogen atom may be substituted with a hydrogen atom, a formyl group, an alkyl group having from 1 to 6 carbon atoms or an acyl group having from 2 to 5 carbon atoms, and there may be a carbonyl group next to this nitrogen atom, The two carbon atoms shared by the two rings constituting $R^2$ are substituted by $R^3$ and $R^4$, respectively. $R^3$ and $R^4$ each represents a hydrogen atom, an alkyl group having from 1 to 4 carbon atoms or an alkoxy group having from 1 to 4 carbon atoms. $R^3$ and $R^4$ may be either on the same side (cis-configuration) or different sides (trans-configuration) of the plane formed by the rings. The bond between the two carbon atoms shared by the two rings may be either a single bond or a double bond.

$R^2$ may further be substituted by 1 to 4 alkyl groups each having from 1 to 6 carbon atoms.

The preferable bicyclic nitrogen-containing heterocyclic substituent include:

2,8-diazabicyclo[4.3.0]nonan-8-yl group and 8-alkylated analogue thereof, such as 8-methyl-, 8-ethyl-, 8-propyl-, 8-isopropyl-, and so forth;

3,7-diazabicyclo[3.3.0]oct-1(5)-ene-3-yl group and 7-alkylated analogue thereof, such as 7-methyl-, 7-ethyl-, 7-propyl-, 7-isopropyl-, and so forth;

3,7-diazabicyclo[3.3.0]octan-3-yl group and 7-alkylated analogue thereof, such as 7-methyl-, 7-ethyl-, 7-propyl-, 7-isopropyl-, and so forth;

3,8-diazabicyclo[4.3.0]non-1(6)-ene-8-yl group and 3-alkylated analogue thereof, such as 3-methyl-, 3-ethyl-, 3-propyl-, 3-isopropyl-, and so forth;

3,8-diazabicyclo[4.3.0]nonan-8-yl group and 3-alkylated analogue thereof, such as 3-methyl-, 3-ethyl-, 3-propyl-, 3-isopropyl-, and so forth;

3-oxo-2,5,8-triaza[4.3.0]nonan-8-yl group and mono- or dialkylated analogue thereof, such as 2-methyl-, 2-ethyl-, 2-propyl-, 2-isopropyl-, 5-methyl-, 5-ethyl-, 5-propyl-, 5-isopropyl-, 2,5-dimethyl-, 2,5-diethyl-, 2,5-dipropyl-, 2,5-diisopropyl-, 2-methyl-5-ethyl-, 2-methyl-5-propyl-, 2-methyl-5-isopropyl-, 2-ethyl-5-methyl-, 2-ethyl-5-methyl-, 2-propyl-5-methyl-, 2-isopropyl-5-methyl-, 2-ethyl-5-propyl-, 2-ethyl-5-isopropyl-, 2-propyl-5-ethyl-, 2-isopropyl-5-ethyl-, 2-propyl-5-isopropyl-, 5-propyl-2-isopropyl-, and so forth;

5-oxo-2,4,8-triaza[4.3.0]nonan-8-yl group and mono- or dialkylated analogue thereof, such as 2-methyl-, 2-ethyl-, 2-propyl-, 2-isopropyl-, 4-methyl-, 4-ethyl-, 4-propyl-, 4-isopropyl-, 2,4-dimethyl-, 2,4-diethyl-, 2,4-dipropyl-, 2,4-diisopropyl-, 2-methyl-4-ethyl-, 2-methyl-4-propyl-, 2-methyl-4-isopropyl-, 2-ethyl-4-methyl-, 2-ethyl-4-methyl-, 2-propyl-4-methyl-, 2-isopropyl-4-methyl-, 2-ethyl-4-propyl-, 2-ethyl-4-isopropyl-, 2-propyl-4-ethyl-, 2-isopropyl-4-ethyl-, 2-propyl-4-isopropyl-, 4-propyl-2-isopropyl-, and so forth;

2-oxa-5,8-diazabicyclo[4.3.0]-nonan-8-yl group or 5-alkylated analogue thereof, such as 8-methyl-, 8-ethyl-, 8-propyl-, 8-isopropyl-, and so forth.

It is particularly preferable that the nitrogen-containing heterocyclic substituent $R^2$ is bonded to the 7-position of the quinolone nucleus through the nitrogen atom thereof. The compound wherein the nitrogen-containing heterocyclic substituent is bonded at the carbon atom thereof is also included within the scope of the present invention.

In cases where a bicyclic nitrogen-containing heterocyclic compound which is used for introducing the bicyclic nitrogen-containing heterocyclic substituent $R^2$ includes stereoisomerism, reaction between a mixture of the stereoisomers and a quinolone compound results in formation of a mixture of diastereomers of a quinolone derivative due to the stereochemical relationship between the introduced bicyclic nitrogen-containing heterocyclic substituent and the 1,2-cis-2-halogenocyclopropyl group at the 1-position. Therefore, in these cases, it is preferable to use a single stereoisomer of the nitrogen-containing heterocyclic compound as a starting material.

In carrying out the reaction for introducing the bicyclic nitrogen-containing heterocyclic substituent to the 7-position of a quinolone nucleus, the nitrogen atom of the heterocyclic ring may be protected with a commonly employed protective group, such as an alkoxycarbonyl group, e.g., a t-butoxycarbonyl group and a 2,2,2-trichloroethoxycarbonyl group; an aralkyloxycarbonyl group, e.g., a benzyloxycarbonyl group, a p-methoxybenzyloxycarbonyl group, and a p-nitrobenzyloxycarbonyl group; an acyl group, e.g., an acetyl group, a methoxyacetyl group, a trifluoroacetyl group, a chloroacetyl group, a pivaloyl group, a formyl group, and a benzoyl group; an alkyl group or an aralkyl group, e.g., a t-butyl group, a benzyl group, a p-nitrobenzyl group, a p-methoxybenzyl group, and a triphenylmethyl group; an ether group, e.g., a methoxymethyl group, a t-butoxymethyl group, a tetrahydropyranyl group, and a 2,2,2-trichloroethoxymethyl group; and a silyl group, e.g., a trimethylsilyl group, an isopropyldimethylsilyl group, a t-butyldimethylsilyl group, a tribenzylsilyl group, and a t-butyldiphenylsilyl group.

The 1,2-cis-2-halogenocyclopropyl group is described hereinafter.

The cyclopropyl group at the $N_1$-position of the compound of the present invention is substituted with a halogen atom, preferably a fluorine atom, which produces an effect of reducing lipophilicity of the whole molecule. The present inventors have thought that distribution of a medicament to the central nervous system and excretion into the bile would be accelerated as the lipophilicity of the compound increases and that the $N_1$-(1,2-cis-2-halogenocyclopropyl)-substituted pyridonecarboxylic acid derivative of the present invention would be less toxic accordingly. The halogen atom on the cyclopropyl group includes a fluorine atom and a chlorine atom, and a fluorine atom is particularly preferred.

The halogen atom and the pyridonecarboxylic acid moiety are preferably in a cis-configuration with respect to the cyclopropane ring. Regardless of stereoisomerism of the bicyclic nitrogen-containing heterocyclic substituent at the 7-position, the cis-2-halogenocyclopropyl moiety at the 1-position gives a pair of antipodes. Each of antipodes was observed to exhibit potent antimicrobial activity and high safety.

Where diastereomers may exist in the compound of formula (I), it is necessary to administer a compound comprising a single diastereomer to humans or animals. The terminology "single diastereomer" as used herein is construed as including not only a compound containing no other diastereomer but a compound containing other diastereomers to such an extent that the whole structure is recognized to be chemically pure. In other words, it is construed as meaning that other diastereomers may exist to some extent as long as such existence gives no substantial influence on physiological activities or physicochemical constants. Moreover, if a compound is present in an isomerically pure state, such a compound is safe to be said "having a single stereoisomerism".

The pyridonecarboxylic acid derivative of the present invention may be either in a free form or a form of an acid addition salt or a salt at the carboxyl group. Acid addition salts include inorganic acid salts, such as hydrochlorides, sulfates, nitrates, hydrobromides, hydroiodides, and phosphates; and organic acid salts, such as acetates, methanesulfonates, benzenesulfonates, toluenesulfonates, citrates, maleates, fumarates, and lactates.

Salts at the carboxyl group include both inorganic salts and organic salts, such as alkali metal salts, e.g., lithium salts, sodium salts, and potassium salts; alkaline earth metal salts, e.g., magnesium salts and calcium salts; ammonium salts; triethylamine salts; N-methylglucamine salts; and tris-(hydroxymethyl)aminomethane salts.

The free pyridonecarboxylic acid derivatives, acid addition salts thereof, and salts thereof at the carboxyl group may be present as a hydrate.

On the other hand, when the carboxylic acid moiety of quinolone derivatives is an ester moiety, they are useful as a synthetic intermediate or a pro-drug (a drug precursor). For example, alkyl esters, benzyl esters, alkyloxyalkyl esters, phenylalkyl esters, and phenyl esters are useful as synthetic intermediates.

Esters which can be used as pro-drugs are esters which are easily cleaved in vivo to give a free carboxylic acid, and include acetoxymethyl esters, pivaloyloxymethyl esters, ethoxycarbonyl esters, choline esters, dimethylaminoethyl esters, 5-indanyl esters, phthalidinyl esters, 5-alkyl-2-oxo-1,3-dioxol-4-yl-methyl esters, and oxoalkyl esters, such as 3-acetoxy-2-oxobutyl esters.

A process for preparing the compounds according to the present invention is explained below by way of an illustrative example for a compound having a quinoline skeleton.

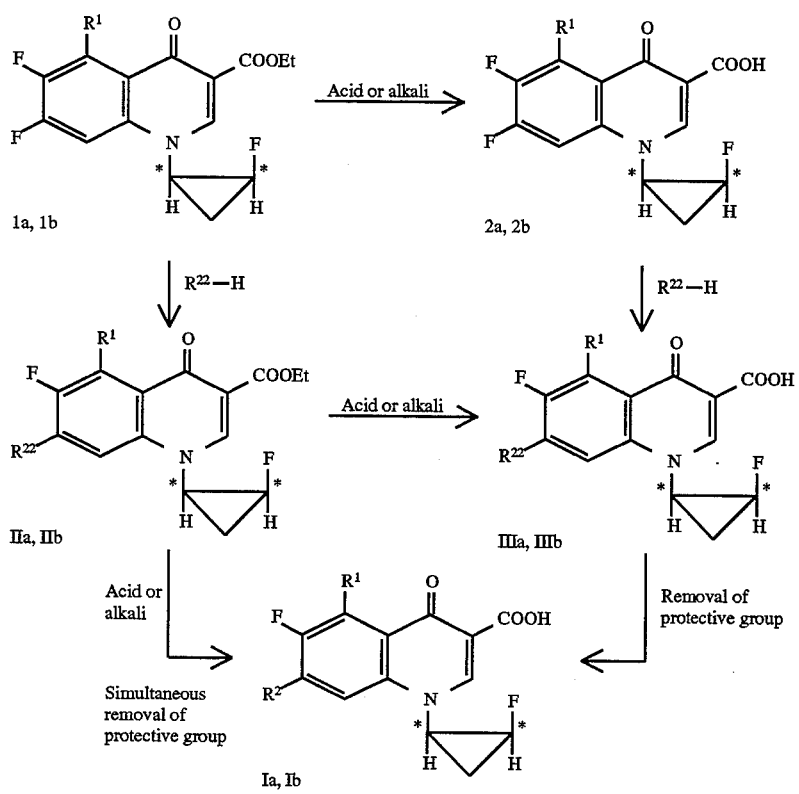

In the scheme above, $R^{22}$ represents the same bicyclic nitrogen-containing heterocyclic substituent as $R^2$ or a protected group thereof.

An optically active, stereoisomerically pure, 1-(1,2-cis-2-fluorocyclopropyl)-6,7-difluoro-4-oxo-1,4-dihydroquinoline-3-carboxylic acid ethyl ester 1a or 1b is hydrolyzed under an acidic or alkaline condition to give a free carboxylic acid derivative 2a or 2b. Compound 2a or 2b is then reacted with a bicyclic nitrogen-containing heterocyclic compound $R^{22}$-H to yield a desired compound IIIa or IIIb. If desired, a protective group in $R^{22}$ is removed under conditions selected according to the protective group to give a desired compound Ia or Ib. The substitution reaction between the quinoline compound and the bicyclic nitrogen-containing heterocyclic compound may be carried out in a solvent, such as dimethyl sulfoxide, pyridine, acetonitrile or 3-methoxybutanol, at a temperature of from room temperature to about 150° C., and preferably from about 40° to about 120° C. The reaction time ranges from about 30 minutes to about 5 hours and the reaction time of from about 30 minutes to about 2 hours usually complete the reaction.

Alternatively, compound 1a or 1b is reacted with the bicyclic nitrogen-containing heterocyclic compound under conditions similar to those described above, and the resulting compound IIa or IIb is hydrolyzed under an acidic or alkaline condition without being isolated and purified and, if necessary, treated to cleave the protective group from $R^{22}$ to yield a desired compound IIIa or IIIb or Ia or Ib.

A stereoisomerically pure cis-2-fluorocyclopropylamine necessary for synthesizing the compound 1a or 1b can be synthesized as follows.

2-Fluorocyclopropanecarboxylic acid is reacted with (R)-(+)-α-methylbenzylamine to give N-[1-(R)-phenylethyl]-1,2-cis-2-fluorocyclopropanecarboxamide. This reaction can be carried out in tetrahydrofuran in the presence of N,N'-carbonyldiimidazole or in accordance with a mixed anhydride method. In the mixed anhydride method, the carboxylic acid is dissolved in an aprotic solvent and reacted with a halogenoformic ester in the presence of a base at a low temperature. The reaction product is then reacted with the above-mentioned benzylamine, and the reaction mixture is treated by a known method to give a carboxamide. The resulting carboxamide is chromatographically separated into each enantiomer of N-[1-(R)-phenylethyl]-1,2-cis-2-fluorocyclopropanecarboxamide.

The solvent to be used in the mixed anhydride method preferably includes aprotic solvents, such as ethers, e.g., diethyl ether, diisopropyl ether, tetrahydrofuran, 1,4-dioxane, and 1,2-dimethoxyethane; halogenated hydrocarbons, e.g., dichloromethane, chloroform, 1,2-dichloroethane, and 1,1,2,2-tetrachloroethane; aromatic hydrocarbons, e.g., benzene, toluene, and xylene; and aliphatic hydrocarbons, e.g., pentane, hexane, heptane, and cyclohexane. Of these solvents, generally employed are tetrahydrofuran, chloroform, etc. In carrying out the reaction, the water contained in the solvent is generally removed beforehand.

The halogen atom in the halogenoformic ester is usually a chlorine atom. The esters include those of methyl, ethyl, 2,2,2-trichloroethyl, phenyl, p-nitrophenyl, benzyl, etc.

The base to be used may be either inorganic or organic. Examples of inorganic bases include hydroxides, carbonates or hydrogencarbonates of alkali metals, such as lithium hydroxide, sodium hydroxide, potassium hydroxide, lithium carbonate, sodium carbonate, potassium carbonate, sodium hydrogencarbonate, and potassium hydrogencarbonate.

Examples of organic bases include trialkylamines, e.g., triethylamine, tripropylamine, tributylamine, and N,N-diisopropylethylamine; dialkylanilines, e.g., diethylaniline and dimethylaniline; and saturated or aromatic heterocyclic compounds, e.g., N-methylmorpholine, pyridine, and N,N-dimethylaminopyridine.

Separation of the produced carboxamide into optical isomers can be performed in a usual manner by silica gel column chromatography, silica gel column chromatography under pressure, preparative TLC, high performance liquid chromatography, and so forth. It is also possible to separate into optical isomers through generally employed separation techniques other than chromatography, such as recrystallization, reprecipitation, and the like.

The thus separated optically active carboxamide compound is led to an optically active cis-2-fluorocyclopropanecarboxylic acid by heating in an acidic condition. The heating is effected by, for example, dissolving the carboxamide in concentrated hydrochloric acid followed by heating. Sulfuric acid, nitric acid, etc. may also be used. The reaction may also be carried out in the presence of a solvent, such as acetic acid, a lower alcohol, etc.

The resulting carboxylic acid compound is subjected to Curtius reaction in the presence of t-butanol to be converted directly to protected cis-1-(t-butoxycarbonylamino)-2-fluorocyclopropane. While this reaction can be carried out conveniently by using diphenylphosphoryl azide, synthesis of the intermediate azide compound is not limited thereto, and usual synthetic processes may be applied.

Starting with the thus obtained stereoisomerically pure cis-2-fluorocyclopropylamine derivative, a quinolone derivative having a cis-fluorocyclopropyl group at the 1-position can be obtained as a single antipode which is then reacted with a bicyclic nitrogen-containing heterocyclic compound as described above to yield a quinolone derivative of the present invention.

The compounds of the present invention have potent antimicrobial activity and are therefore useful as medicaments for humans, animals or fishes, agricultural chemicals, or food preservatives.

For use as medicaments for humans, the dose of the compound is in the range of from 50 mg to 1 g, and preferably from 100 mg to 300 mg, per day for adults.

For veterinary use, the dose is generally in the range of from 1 to 200 mg, and preferably from 5 to 100 mg, per kg of body weight per day while varying depending on the purpose of administration (for therapy or for prevention), the kind and the size of the animal, the kind of the pathogenic organisms, and the symptom.

The above-mentioned daily dose is given once a day or in 2 to 4 divided doses. If necessary, a daily dose may exceed the above-specified range.

The compounds according to the present invention are active on a very broad range of microorganisms causing various infectious diseases and effective to prevent, alleviate or cure diseases caused by these pathogenes.

Examples of bacteria or bacterium-like microorganisms on which the compounds of the present invention are effective include staphylococci, Streptococcus pyogenes, Streptococcus haemolyticus, enterococci, Streptococcus pneumoniae, peptostreptococci, Neisseria gonorrhoeae, Escherichia coli, Citrobacter sp., Shigella sp., Klebsiella pneumoniae, Enterobacter sp., Serratia sp., Proteus sp., Pseudomonas aeruginosa, Haemophilus influenzae, Acinetobacter sp., Campylobacter sp., and Chlamydozoon trachomatis.

Diseases which are caused by these pathogenes include folliculitis, furuncle, carbuncle, erysipelas, phlegmon, lymphangitis/lymphadenitis, felon, subcutaneous abscess, spiradenitis, acne conglobata, infectious atheroma, perianal abscess, mastadenitis, superficial secondary infections after trauma, burn or surgery trauma, pharyngolaryngitis, acute bronchitis, tonsillitis, chronic bronchitis, bronchiectasis, diffuse panbronchiolitis, secondary infections of chronic respiratory diseases, pneumonia, pyelonephritis, cystitis, prostatitis, epididymitis, gonococcal urethritis, non-gonococcal urethritis, cholecystitis, cholangitis, bacillary dysentery, enteritis, adnexitis, intrauterine infections, bartholinitis, blepharitis, hordeolum, dacryocystitis, tarsadenitis, keratohelcosis, otitis media, sinusitis, paradentosis, pericoronitis, gnathitis, peritonitis, endocarditis, sepsis, meningitis, and skin infections.

The compounds of the present invention are also effective on various microorganisms causing veterinary diseases, such as those belonging to the genera Escherichia, Salmonella, Pasteurella, Haemophilus, Bordetella, Staphylococcus, and Mycoplasma. Illustrative examples of the veterinary diseases include those of fowl, such as colibacillosis, pullorum disease, arian paratyphoid, fowl cholera, infectious coryza, staphylomycosis, and mycoplasmosis; those of pigs, such as colibacillosis, salmonellosis, pasteurellosis, hemophilus infections, atrophic rhinitis, exudative epidermitis, and mycoplasmosis; those of cattle, such as colibacillosis, salmonellosis, hemorrhagic septicemia, mycoplasmosis, bovine contagious pleuropneumonia, and bovine mastitis; those of dogs, such as colisepsis, salmonellosis, hemorrhagic septicemia, pyometra, and cystitis; those of cats, such as exudative pleurisy, cystitis, chronic rhinitis, and hemophilus infections; and those of kittens, such as bacterial diarrhea and mycoplasmosis.

Dosage forms of pharmaceutical antimicrobial preparations containing the compound of the present invention are appropriately selected according to the administration route and can be prepared by conventional preparation methods. Examples of dosage forms for oral administration include tablets, powders, granules, capsules, solutions, syrups, elixirs, and oily or aqueous suspensions.

Injectable preparations may contain adjuvants, such as stabilizers, antiseptics, and solubilizers. The injectable solution which may contain these adjuvants may be put into a container and solidified by, for example, lyophilization to prepare a solid preparation which is dissolved on use. The container may contain either a single dose or multiple doses.

Preparations for external application include solutions, suspensions, emulsions, ointments, gels, creams, lotions, and sprays.

Solid preparations may contain, in addition to the active compound, pharmaceutically acceptable additives. For example, the active compound is mixed with additives selected according to necessity from among fillers, bulking agents, binders, disintegrators, absorption accelerators, wetting agents, and lubricants and formulated into solid preparations.

Liquid preparations include solutions, suspensions, and emulsions. They may contain adjuvants, such as suspending agents, emulsifiers, and so forth.

The compound can be administered to animals orally either directly or by mixing with feedstuff, or in a dissolved form directly given to animals or by mixing with water or feedstuff or non-orally by injection.

For veterinary use, the compound can be formulated into powders, fine granules, soluble powders, syrups, solutions, and injections according to the customary methods in the art.

The present invention will now be illustrated by way of Formulation Examples, Reference Examples, and Examples, but the present invention should not be construed as being limited thereto. All the percents are by weight unless otherwise indicated. The antibacterial activity assays were performed by the method specified by Japan Society of Chemotherapy (*Chemotherapy* 29(1), 76 (1981), and the results are summarized in Table 1 in terms of minimum inhibitory concentration (MIC).

FORMULATION EXAMPLE 1

Capsules

| | |
|---|---|
| Compound of Example 2 | 100.0 mg |
| Corn starch | 23.0 mg |
| CMC.CA | 22.5 mg |
| Hydroxymethyl cellulose | 3.0 mg |
| Magnesium stearate | 1.5 mg |
| Total: | 150.0 mg |

FORMULATION EXAMPLE 2

Solution

| | |
|---|---|
| Compound of Example 2 | 1–10 g |
| Acetic acid or sodium hydroxide | 0.5–2 g |
| Ethyl p-hydroxybenzoate | 0.1 g |
| Purified water | 88.9–98.4 g |
| Total: | 100 g |

FORMULATION EXAMPLE 3

Powder for Mixing with Feed

| | |
|---|---|
| Compound of Example 2 | 1–10 g |
| Corn starch | 98.5–89.5 g |
| Light anhydrous silicic acid | 0.5 g |
| Total: | 100 g |

REFERENCE EXAMPLE 1

N-[1-(R)-Phenylethyl]-1,2-cis-2-fluorocyclopropanecarboxamide 4a, 4b 1-1. Carbonyldiimidazole Method:

In 30 ml of tetrahydrofuran (hereinafter abbreviated as THF) was dissolved 1.0 g of cis-2-fluorocyclopropanecarboxylic acid, and 1.78 g of N,N'-carbonyldiimidazole was added thereto, followed by stirring at room temperature for 1 hour. To the mixture was further added 1.45 g of (R)-(+)-α-methylbenzylamine, and the mixture was stirred for further 2 hours. The solvent was removed under reduced pressure, and a residue was extracted with chloroform. The extract was washed successively with a 10% citric acid aqueous solution and water and dried over anhydrous sodium sulfate, and the solvent was removed under reduced pressure. The residual viscous oily substance was subjected to high performance liquid chromatography for separation into each stereoisomer. Each stereoisomer was recrystallized from diisopropyl ether to give compounds 4a and 4b.

Conditions for Separation:

Column: Nucleosil 50-5 (20 mm (ID)×250 mm (L)), produced by Senshu Scientific Co., Ltd.; Senshu Pack SSC silica, 782-IN)

Solvent: Ethyl acetate/THF (9:1 by volume)

Flow rate: 9.0 ml/min

Retention time: 11 min for compound 4a
  13 min for compound 4b

Compound 4a:

Melting point: 108° C. Elementary analysis, for $C_{12}H_{14}FNO$: Calcd.: C 69.55; H 6.81; N 6.76 Found: C 69.31; H 7.01; N 6.65 $[\alpha]_D$: +61.96° (c=0.965; chloroform) $^1$H-NMR (CDCl$_3$) δ ppm: 0.92–1.34 (2H, m), 1.50 (3H, d, J=7Hz), 1.50–1.96 (1H, m), 4.68 (1H, dm, J=64Hz), 5.14 (1H, m), 7.4 (5H, s)

Compound 4b:

Melting point: 102° C. Elementary analysis, for $C_{12}H_{14}FNO$: Calcd.: C 69.55; H 6.81; N 6.76 Found: C 69.45; H 6.87; N 6.70 $[\alpha]_D$: +143.61° (c=0.830; chloroform) $^1$H-NMR (CDCl$_3$) δ ppm: 0.98–1.34 (2H, m), 1.52 (3H, d, J=7Hz), 1.64–1.96 (1H, m), 4.58 (1H, dm, J=66Hz), 5.24 (1H, m), 7.40 (5H, m)

1-2. Mixed Anhydride Method:

In 50 ml of THF were dissolved 4.19 g of 2-fluorocyclopropanecarboxylic acid (a cis-trans mixture) and 4.07 g of triethylamine, and the solution was cooled to −10° C. To the solution was added dropwise a solution of 4.73 g of ethyl chloroformate in 20 ml of THF and, after stirring for 10 minutes, a solution of 4.88 g of (R)-(+)-α-methylbenzylamine in 30 ml of THF was further added thereto dropwise at that temperature, followed by stirring at room temperature for 15 hours. The solvent was removed under reduced pressure, and a residue was extracted with benzene. The extract was washed successively with a 10% citric acid aqueous solution, a 1N sodium hydroxide aqueous solution, and water and dried over anhydrous sodium sulfate. The solvent was removed under reduced pressure, and the residual pale yellow oily substance was purified by silica gel column chromatography using a mixture of benzene and ethyl acetate as an eluent to give compounds 4a and 4b.

REFERENCE EXAMPLE 2

(−)-Cis-2-Fluorocyclopropanecarboxylic Acid 5a

In 15 ml of concentrated hydrochloric acid was dissolved 530 mg of amide compound 4a, and the solution was heated to 100° to 110° C. with stirring for 5 hours. To the reaction mixture was added 20 ml of water, and the mixture was extracted with ethyl acetate. The extract was extracted with a sodium hydrogencarbonate aqueous solution and washed with ethyl acetate. The aqueous layer was adjusted to pH 5 with concentrated hydrochloric acid and extracted with ethyl acetate. The extract was dried over anhydrous sodium sulfate, and the solvent was removed under reduced pressure to yield the titled compound as a pale yellow oily substance.

$[\alpha]_D$: −23.13° (c=1.020, chloroform) $^1$H-NMR (CDCl$_3$) δ ppm: 1.0–1.42 (1H, m), 1.60–2.10 (2H, m), 4.82 (1H, dm, J=65Hz), 12.0 (1H, s)

REFERENCE EXAMPLE 3

(+)-Cis-2-Fluorocyclopropanecarboxylic Acid 5b

In 30 ml of concentrated hydrochloric acid was dissolved 1.65 g of amide compound 4b, and the solution was heated at 100° to 110° C. with stirring for 5 hours. The reaction mixture was adjusted to pH 8–9 with sodium hydrogencarbonate and washed with chloroform. The aqueous layer was adjusted to pH 4 with concentrated hydrochloric acid and extracted with ethyl acetate. The extract was dried over anhydrous sodium sulfate, and the solvent was removed under reduced pressure to yield the titled compound as a pale yellow oily substance.

[α]$_D$: +21.56° (c=1.113, chloroform) $^1$H-NMR (CDCl$_3$) δ ppm: 1.0–1.42 (1H, m), 1.56–1.98 (2H, m), 4.76 (1H, dm, J=66Hz), 11.32 (1H, s)

REFERENCE EXAMPLE 4

(+)-Cis-1-(t-butoxycarbonylamino)-2-fluorocyclopropane 6a

In 5 ml of t-butanol were dissolved 200 mg of carboxylic acid compound 5a obtained in Reference Example 2, 603 mg of diphenylphosphoryl azide, and 203 mg of triethylamine, and the solution was heated under reflux for 4.5 hours. The solvent was removed under reduced pressure, and a residue was extracted with chloroform. The extract was washed with a 10% citric acid aqueous solution, a 2% sodium hydroxide aqueous solution, and water, and dried over anhydrous sodium sulfate. The solvent was removed under reduced pressure, and a residue was subjected to silica gel column chromatography using chloroform as an eluent to yield the titled compound as a colorless crystal.

Melting point: 73° C. [α]$_D$: 65.57° (c=0.610, chloroform) $^1$H-NMR (CDCl$_3$) δ ppm: 0.6–1.3 (2H, m), 1.46 (9H, s), 2.50–2.76 (1H, m), 4.62 (1H, dm, J=65Hz), 4.5–5.0 (1H, broad)

REFERENCE EXAMPLE 5

(−)-Cis-1-(t-butoxycarbonylamino)-2-fluorocyclopropane 6b

In 6 ml of t-butanol were dissolved 265 mg of carboxylic acid compound 5b obtained in Reference Example 3, 800 mg of diphenylphosphoryl azide, and 270 mg of triethylamine. The solution was worked up in the same manner as in Reference Example 4 to yield the titled compound as a colorless crystal.

Melting point: 63° C. [α]$_D$: −60.27° (c=0.740, chloroform) $^1$H-NMR (CDCl$_3$) δ ppm: 0.66–1.3 (2H, m), 1.46 (9H, s), 2.48–2.74 (1H, m), 4.58 (1H, dm, J=65Hz), 4.6–5.1 (1H, broad)

The product was identified to be (1R,2S)-1-(t-butoxycarbonylamino)-2-fluorocyclopropane from X-ray analysis of the quinolone derivative derived therefrom.

REFERENCE EXAMPLE A

Ethyl (+)-2-[[(1,2-Cis-2-fluoro-1-cyclopropyl)amino]methylene]-3-oxo-3-(3-chloro-2,4,5-trifluorophenyl)propionate A mixture of 1.5 g of ethyl 3-chloro-2,4,5-trifluorobenzoylacetate, 6 ml of ethyl orthoformate, and 10 ml of acetic anhydride was heated at 110° to 120° C. with stirring for 1.5 hours. The reaction mixture was concentrated to dryness under reduced pressure, and a residue was dissolved in 10 ml of dichloromethane.

Ten milliliters of trifluoroacetic acid was cooled with ice, and 1.12 g of (−)-cis-1-(t-butoxycarbonylamino)-2-fluorocyclopropane 6b was dissolved therein. The solution was stirred at room temperature for 20 minutes, followed by concentration to dryness under reduced pressure. A residue was suspended in 20 ml of dichloromethane and cooled with ice, and 2.0 g of triethylamine was added thereto, followed by stirring for 20 minutes. The mixture was added thereto, and the whole was stirred for 1 hour. The mixture was washed with water, dried over anhydrous sodium sulfate, and the solvent was removed under reduced pressure. A residue was subjected to a flash column and eluted with a mixture of benzene and ethyl acetate (4:1 by volume). From a fraction containing the product, the solvent was removed under reduced pressure, and a residue was washed with diisopropyl ether-n -hexane to yield 1.74 g of the titled compound as a crystal.

Melting point: 99°–100° C. [α]$_D$: +6.70° (c=0.895, chloroform) Elementary analysis, for C$_{15}$H$_{12}$ClF$_4$NO$_3$: Calcd. (%): C 49.26; H 3.31; N 3.83 Found (%): C 49.41; H 3.60; N 4.06 $^1$H-NMR (CDCl$_3$) δ ppm: 0.95 and 1.08 (3H, 1:2.5, each t, J=7Hz), 1.0–1.5 (2H, m), 2.8–3.15 (1H, m), 4.03 and 4.07 (2H, 1:2.5, each q, J=7Hz), 4.78 (1H, dm, J=65Hz), 7.13 (1H, ddd, J=5.9, 8.6, 9.5Hz), 8.20 and 8.25 (1H, 1:2.5, each d, J=14Hz)

REFERENCE EXAMPLE B

Ethyl (−)-8-Chloro-6,7-difluoro-1-(1,2-cis-2-fluoro-1-cyclopropyl)-4-oxo-1,4-dihydroquinoline-3-carboxylate Five-hundred sixty milligrams of 60% sodium hydride were washed twice with anhydrous n-hexane and suspended in 10 ml of anhydrous dioxane. The suspension was added to a solution of 1.70 g of ethyl (+)-2-[[(1,2-cis-2-fluoro-1-cyclopropyl)amino]methylene]-3-oxo-3-(3-chloro-2,4,5-trifluorophenyl)propionate in 20 ml of anhydrous dioxane; followed by stirring at room temperature for 2 hours. The solvent was removed under reduced pressure, and 0.1N hydrochloric acid was added to a residue. The thus formed crystal was collected by filtration, washed with water and diethyl ether, and dried under reduced pressure to yield 1.44 g of the titled compound as a colorless crystal. This compound was identified to be ethyl 8-chloro-6,7-difluoro-1-[(1R,2S)-2-fluorocyclopropyl]-1,4-dihydro-4-oxoquinoline-3-carboxylate by X-ray analysis.

Melting point: 174° C. [α]$_D$: −45.3° (c=1.05, chloroform) Elementary analysis, for C$_{15}$H$_{11}$ClF$_3$NO$_3$: Calcd. (%): C 52.12; H 3.21; N 4.05 Found (%): C 51.80; H 3.45; N 4.15 $^1$H-NMR (CDCl$_3$) δ ppm: 1.40 (3H, t, J=7Hz), 1.4–1.9 (2H, m), 4.08 (1H, 4.39 (2H, q, J=7Hz), 4.90 (1H, dm, J=65Hz), 8.24 (1H, dd, J=10, 11Hz) IR (KBr): ν$_{max}$cm$^{-1}$: 3100, 2998, 1731, 1638, 1614, 1470, 1317

REFERENCE EXAMPLE C (−)-8-Chloro-6,7-difluoro-1-(1,2-cis-2-fluoro-1-cyclopropyl)-4-oxo-1,4-dihydroquinoline-3-carboxylic Acid A mixture of 1.40 g of ethyl (−)-8-chloro-6,7-difluoro-1-(1,2-cis-2-fluoro-1-cyclopropyl)-4-oxo-1,4-dihydroquinoline-3-carboxylate and 10 ml of concentrated hydrochloric acid was heated at 110° C. with stirring for 2.5 hours. To the reaction mixture was added 50 ml of water, and a precipitated crystal was collected by filtration, washed with water and diethyl ether, and dried under reduced pressure to yield 1.16 g of the titled compound as a colorless crystal.

Melting point: 177°–182° C. [α]$_D$: −26.8° (c=0.90, chloroform) Elementary analysis, for C$_{13}$H$_7$ClF$_3$NO$_3$: Calcd. (%): C 49.16; H 2.22; N 4.41 Found (%): C 49.28; H 2.40; N 4.66 $^1$H-NMR (CDCl$_3$) δ ppm: 1.3–2.0 (2H, m), 4.12–4.34 (1H, m), 4.95 (1H, dm, J=63Hz), 8.27 (1H, dd, J=8, 8Hz), 8.87 and 8.89 (1H, each s, split, 1:1)

REFERENCE EXAMPLE 6

6-Benzyl-5,7-dihydro-5,7-dioxopyrrolo[3,4-b]pyridine

To 100 g of 2,3-pyridinedicarboxylic acid was added dropwise 170 ml of acetic anhydride at room temperature, and the mixture was heated up to 110° C., and stirred for 4 hours. After completion of the reaction, the solvent was removed under reduced pressure. To a residue was added 200 ml of diethyl ether, and a precipitated crystal was collected by filtration and washed with diethyl ether (100 ml×4) to yield 86 g of an acid anhydride compound. To the product was added dropwise 76 ml of benzylamine while cooling with ice, and the mixture was stirred at 180° C. for 30 minutes. To the reaction mixture was added dropwise 170 ml of acetic anhydride while cooling with ice, followed by stirring at 110° C. for 2 hours. After completion of the reaction, the reaction mixture was allowed to cool, and 500 ml of ethanol was added thereto. The thus formed crystal was collected by filtration and washed with ethanol (100 ml×3) to yield 89.4 g of the titled compound.

Melting point: 163°–165° C. (recrystallized from ethanol)
$^1$H-NMR (400 MHz, DMSO-d$_6$) δ ppm: 4.28 (2H, s), 7.26–7.34 (5H, m), 7.80 (1H, dd, J=7.8, 5.4Hz), 8.31 (1H, dd, J=7.8, 1.5Hz), 8.99 (1H, dd, J=5.4, 1.5Hz)

REFERENCE EXAMPLE 7

6-Benzyl-5,7-dioxo-octahydropyrrolo[3,4-b]pyridine

To 10 g of 6-benzyl-5,7-dihydro-5,7-dioxopyrrolo[3,4-b]pyridine were added 84 ml of 2-methoxyethanol and 1.5 g of a ruthenium-on-carbon catalyst, and hydrogenation was conducted under a pressurized hydrogen gas atmosphere at 4.5 kg/cm$^2$ for 22 hours. The catalyst was removed by filtration, and the filtrate was concentrated. To the concentrate were added 84 ml of 2-methoxyethanol and 2 g of a palladium-on-charcoal catalyst, and hydrogenation was conducted under a pressurized hydrogen gas atmosphere at 4.5 kg/cm$^2$ for 7 hours. The catalyst was removed by filtration, and the filtrate was concentrated to yield 10.4 g of the titled compound. Throughout the hydrogenation, the reaction vessel was heated by a tungsten lamp.

$^1$H-NMR (400 MHz, CDCl$_3$) δ ppm: 1.52 (2H, dt, J=11.8, 5.9Hz), 1.65 (1H, dt, J=6.8, 13.4Hz), 1.97 (1H, dt, J=5.9, 13.4Hz), 2.68 (1H, dt, J=11.8, 5.9Hz), 2.79 (1H, dt, J=11.8, 5.9Hz), 2.86 (1H, dd, J=6.8, 7.3Hz), 3.85 (1H, d, J=7.3Hz), 4.65 (2H, s), 7.26–7.34 (5H, m)

REFERENCE EXAMPLE 8

6-Benzyl-octahydropyrrolo[3,4-b]pyridine

In 50 ml of anhydrous THF was suspended 4.9 g of lithium aluminum hydride, and a solution of 3 g of 6-benzyl-5,7-dioxo-octahydropyrrolo[3,4-b]pyridine in 50 ml of anhydrous THF was added thereto dropwise with stirring while cooling with ice. After the addition, the reaction mixture was heated under reflux for 6 hours. After completion of the reaction, 4.9 ml of water, 4.9 ml of aqueous ammonia, and 15 ml of water were added to the reaction mixture in this order while cooling with ice, followed by stirring for 30 minutes. The reaction mixture was filtered through Celite®, and the filter cake was washed with THF (100 ml×4). The combined filtrate and washings were dried over anhydrous sodium sulfate and concentrated to yield 2.49 g of the titled compound as an oily substance.

$^1$H-NMR (400 MHz, CDCl$_3$) δ ppm: 1.31–1.4 (2H, m), 1.46–1.65 (2H, m), 2.02 (1H, br s), 2.12–2.20 (1H, m), 2.47–2.54 (2H, m), 2.56 and 2.69 (each 1H, each t, J=8.8Hz), 2.78 (1H, dd, J=5.4, 10.3Hz), 2.91 (1H, dt, J=12.7, 3.9Hz), 3.15 (1H, dt, J=5.4, 2.0Hz), 3.63 and 3.69 (each 1H, each d, J=12.7Hz), 7.14–7.28 (5H, m)

REFERENCE EXAMPLE 9

6-Benzyl-1-t-butoxycarbonyloctahydropyrrolo[3,4-b]pyridine

In 25 ml of acetonitrile was dissolved 2.49 g of 6-benzyl-octahydropyrrolo[3,4-b]pyridine, and a solution of 3.75 g of Boc2O in 25 ml of acetonitrile was added thereto dropwise at room temperature, followed by stirring at that temperature for 14 hours. After completion of the reaction, 200 ml of ethyl acetate was added to the reaction mixture, and the mixture was washed with 100 ml of a saturated sodium hydrogencarbonate aqueous solution and dried over anhydrous sodium sulfate. The solvent was removed under reduced pressure, and a residue was subjected to column chromatography on Florisil® using a 4:1 (by volume) mixture of n-hexane and ethyl acetate as an eluent to yield 2.86 g of the titled compound as an oily substance.

$^1$H-NMR (400 MHz, CDCl$_3$) δ ppm: 1.44 (9H, s), 1.38–1.56 (2H, m), 1.59–1.73 (2H, m), 2.11–2.18 (1H, m), 2.45–2.55 (1H, m), 2.55–2.70 (1H, m), 2.70–2.85 (3H, m), 3.63 and 3.70 (each 1H, each d, J=13.2Hz), 3.88 and 4.60 (each 1H, each br s), 7.23–7.32 (5H, m)

REFERENCE EXAMPLE 10

1-t-Butoxycarbonyloctahydropyrrolo[3,4-b]pyridine

In 50 ml of ethanol was dissolved 2.86 g of 6-benzyl-1-t-butoxycarbonyloctahydropyrrolo[3,4-b]pyridine, and 500 mg of 5% palladium-on-carbon was added thereto. While the reaction vessel was heated by a tungsten lamp, hydrogenation was conducted under a pressurized hydrogen gas atmosphere of 4 kg/cm$^2$ for 1.5 hours. After completion of the reaction, the catalyst was removed by filtration, and the filtrate was concentrated to yield 1.98 g of the titled compound as an oily substance.

$^1$H-NMR (400 MHz, CDCl$_3$) δ ppm: 1.46 (9H, s), 1.40–1.52 (2H, m), 1.66–1.71 (2H, m), 2.07–2.10 (1H, m), 2.71–2.80 (3H, m), 3.09–3.19 (2H, m), 3.91 and 4.50 (each 1H, each br s)

REFERENCE EXAMPLE 11

[4aS,7aS]-6-Benzyloctahydropyrrolo[3,4-b]pyridine

In hot ethanol were dissolved 16.4 g of 6-benzyloctahydropyrrolo[3,4-b]pyridine and 11.3 g of D-(−)-tartaric acid, and acetone was added to the solution. The precipitated crystal was collected by filtration and recrystallized three times from a mixture of methanol and acetonitrile to yield 7.1 g of a tartrate. The tartrate was dissolved in 100 ml of a 1N sodium hydroxide aqueous solution and the mixture was extracted with chloroform (100 ml×3). The extract was dried over anhydrous sodium sulfate, and the solvent was removed under reduced pressure to yield 3.49 g of the titled compound.

REFERENCE EXAMPLE 12

(4aS,7aS)-6-Benzyl-1-t-butoxycarbonyloctahydropyrrolo[3,4-b]pyridine

In 100 ml of acetonitrile was dissolved 3.49 g of the optically active (4aS,7aS)-6-benzyloctahydropyrrolo[3,4-b]pyridine obtained in Reference Example 11, and a solution of 4.27 g of Boc$_2$O in 30 ml of acetonitrile was added thereto dropwise under ice-cooling, followed by stirring at room temperature for 14 hours. After completion of the reaction, the solvent was removed under reduced pressure, and a residue was subjected to column chromatography on Florisil® using a 4:1 (by volume) mixed solution of n-hexane and ethyl acetate as an eluent to yield 4.0 g of the titled compound as an oily substance from the eluate. The product was found to have optical purity of 99.6% ee by high performance liquid chromatography conducted under the following conditions.

Column: Daicel Chiralcel OD, 25 cm×0.46 cm

Mobile phase: n-hexane:isopropyl alcohol=99:1 by volume

Flow rate: 0.2 ml/min

Temperature: room temperature

Detection: UV (254 nm)

Retention time: 23.49 mins for (R,R)-compound
26.59 mins for (S,S)-compound

REFERENCE EXAMPLE 13

(4aS,7aS)-1-t-Butoxycarbonyloctahydropyrrolo[3,4-b]pyridine

In 130 ml of ethanol was dissolved 3.86 g of (4aS,7aS)-6-benzyl-1-t-butoxycarbonyloctahydropyrrolo[3,4-b]pyridine, and 1 g of 5% palladium-on-carbon was added thereto. While the reaction vessel was heated by a tungsten lamp, hydrogenation was conducted under pressurized hydrogen gas atmosphere of 4 kg/cm² for 4 hours. After completion of the reaction, the catalyst was removed by filtration, and the filtrate was concentrated to give 2.75 g of the titled compound.

EXAMPLE 1

7-([S,S]-2-t-Butoxycarbonyl-2,8-diazabicyclo[4.3.0]nonan-8-yl)-8-chloro-6-fluoro-1-[(1R,2S)-2-fluorocyclopropyl]-1,4-dihydro-4-oxoquinoline-3-carboxylic Acid In 20 ml of acetonitrile were dissolved 344 mg of 8-chloro-6,7-difluoro-1-[(1R,2S)-2-fluorocyclopropyl]-1,4-dihydro-4-oxoquinoline-3-carboxylic acid, 490 mg of (S,S)-1-t-butoxycarbonyloctahydropyrrolo[3,4-b]pyridine (also termed "(S,S)-2-t-butoxycarbonyl-2,8-azabicyclo[4.3.0]nonane"), and 1 ml of triethylamine, and the solution was heated under reflux for 5 hours. After completion of the reaction, the solvent was removed under reduced pressure. To a residue was added 30 ml of water, followed by extracting with chloroform (30 ml×4). The combined organic layer was washed with 100 ml of a 10% citric acid aqueous solution and dried over anhydrous sodium sulfate. The solvent was removed under reduced pressure, and a residue was recrystallized from acetonitrile to yield 317 mg of the titled compound.

¹H-NMR (400 MHz, CDCl₃) δ ppm: 1.49 (9H, s), 1.46–1.57 (4H, m), 1.70–1.85 (2H, m), 2.23–2.29 (1H, m), 2.83–2.89 (1H, m), 3.14–3.18 (1H, m), 3.35–3.45 (1H, m), 3.90–3.97 (1H, m), 4.08–4.18 (2H, m), 4.23–4.32 (1H, m), 4.73–4.95 (2H, m), 7.98 (1H, d, J=13.2Hz), 8.78 (1H, s), 14.51 (1H, br s).

EXAMPLE 2

8-Chloro-7-([S,S]-2,8-diazabicyclo[4.3.0]nonan-8-yl)-8-chloro-6-fluoro-1-[(1R,2S)-2-fluorocyclopropyl]-1,4-dihydro-4-oxoquinoline-3-carboxylic Acid

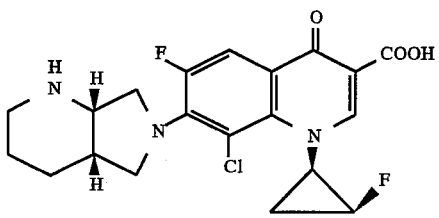

A mixture of 314 mg of 7-([S,S]-2-t-butoxycarbonyl-2,8-diazabicyclo[4.3.0]nonan-8-yl)-8-chloro-6-fluoro-1-[(1R,2S)-2-fluorocyclopropyl]-1,4-dihydro-4-oxoquinoline-3-carboxylic acid and 10 ml of trifluoroacetic acid was stirred at room temperature for 4 hours. After completion of the reaction, trifluoroacetic acid was removed under reduced pressure, and a residue was dissolved in a 1N sodium hydroxide aqueous solution so as to have a pH of 12. The solution was adjusted to pH 7.4 with hydrochloric acid and extracted with chloroform (30 ml×4). The combined organic layer was dried over anhydrous sodium sulfate, and the solvent was removed under reduced pressure. A residue was recrystallized from a mixture of ethanol and chloroform to yield 173 mg of the titled compound as a needle-like crystal.

Melting point: 240°–241° C. (with decomposition) [α]$_D^{25}$: −270.0° (c=0.50, 1N NaOH) Elementary analysis, for C₂₀H₂₀ClF₂N₃O₃: Calcd. (%): C 56.68; H 4.76; N 9.91 Found (%): C 56.69; H 4.75; N 9.87 ¹H-NMR (400 MHz, 0.1N NaOD) δ ppm: 1.23–1.40 (1H, m), 1.50–1.80 (3H, m), 1.70–1.85 (2H, m), 2.35–2.47 (1H, m), 2.52–2.63 (1H, m), 2.90–3.00 (1H, m), 3.25–3.35 (1H, m), 3.36–3.43 (2H, m), 4.10–4.25 (3H, m), 4.93–5.18 (1H, m), 7.78 (1H, d, J=13.6Hz), 8.43 (1H, s).

When analyzed by silica gel thin layer chromatography (developing solution: chloroform:methanol:water=7:3:1 by volume), the compound of the present invention had an Rf value of 0.26. On the other hand, a compound having a mere cyclopropyl group with no fluorine atom at the N₁-position thereof (i.e., the compound of JP-A-2-69474, the term "JP-A" means an "unexamined published Japanese patent application") had an Rf value of 0.38. The comparison proves the compound of the present invention less lipophilic and thereby superior to the latter.

EXAMPLE 3

5-Amino-7-[(S,S)-2,8-diazabicyclo[4.3.0]nonan-8-yl]-6,8-difluoro-1-[(1R,2S)-2-fluorocyclopropyl]-1,4-dihydro-4-oxoquinoline-3-carboxylic acid

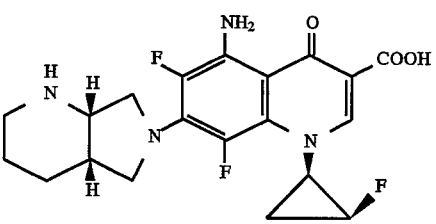

A solution of 158 mg of 5-amino-6,7,8-difluoro-1-[(1R,2S)-2-fluorocyclopropyl]-1,4-dihydro-4-oxoquinoline-3- carboxylic acid (EP-A-0 341 493), 226 mg of 2-tert-butoxycarbonyl-(S,S)-2,8-diazabicyclo[4.3.0]nonane, 1 ml of triethylamine in 5 ml of acetonitrile was heated under reflux for 22 hours. The solvent was removed under reduced pressure and a residue was dissolved in 50 ml of chloroform. The solution was washed by 10% citric acid aqueous solution (200 ml, once) and saturated sodium chloride aqueous solution (100 ml, once). The solution was dried over anhydrous sodium sulfate. The solvent was removed under reduced pressure. A residue was dissolved in 10 ml of trifluoroacetic acid, and the solution was stirred at room temperature for 5 hours. Trifluoracetic acid was removed under reduced pressure and to a residue was added 1N NaOH till the pH became pH 12. To the solution was added hydrochloric acid till the pH became 7.4. The solution was extracted with four 50 ml portions of chloroform. The extract was dried over anhydrous sodium sulfate. The solvent was removed under reduced pressure and a residue was dissolved in ethanol. The solution was stood in a deep freezer. A resulting crystalline product was collected and dried to yield 118 mg of the titled compound.

Melting point: 145°–149° C. $[\alpha]_D^{25}$: −271.30° (c=0.12, MeOH) $^1$H-NMR (400 MHz, 0.1N NaOD) δ ppm: 1.45–1.79 (6H, m), 2.26–2.38 (1H, m), 2.54–2.63 (1H, m), 2.88–2.94 (1H, m), 3.29–3.58 (3H, m), 3.79–4.02 (3H, m), 4.85–5.08 (1H, m), 8.18 (1H, s). Elementary analysis, for $C_{20}H_{21}F_3N_4O_3 \cdot \frac{1}{4}H_2O$; Calcd. (%): C 56.27; H 5.08; N 13.12 Found (%): C 56.66; H 5.10; N 12.88

EXAMPLE 4

7-[(S,S)-2,8-diazabicyclo[4.3.0]nonan-8-yl]-6-fluoro-1-[(1R,2S)-2-fluorocyclopropyl]-8-methyl-1,4-dihydro-4-oxoquinoline-3-carboxylic acid

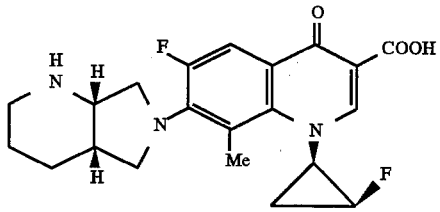

A solution of 590 mg of 6,7,8-difluoro-1-[(1R,2S)-2-fluorocyclopropyl]-1,4-dihydro-4-oxoquinoline-3-carboxylic acid BF2-chelate (obtained by a reaction of 6,7,8-difluoro-1-[(1R,2S)-2-fluorocyclopropyl]-1,4-dihydro-4-oxoquinoline-3-carboxylic acid (EP-A-0 341 493) and boron trifluoride etherate), 798 mg of 2-tert-butoxycarbonyl-(S,S)-2,8-diazabicyclo[4.3.0]nonan, 0.49 ml of triethylamine in 6 ml of sulfolane was stirred at room temperature for 10 days. To the solution was added 50 ml of 10% citric acid aqueous solution and a resulting crystal was collected by filtration. The crystalline was dissolved in 100 ml of 90% methanol and 2 ml of triethylamine. The mixture was heated under reflux for 3 hours. The solvent was removed under reduced pressure and a residue was dissolved in 6 ml of trifluoroacetic acid. The solution was stirred at room temperature for 3 hours. The solvent was removed under reduced pressure. To a residue was added 50 ml of 1N hydrochloric acid, and the mixture was washed by 50 ml of chloroform. To the aqueous layer was added 1N sodium hydroxide aqueous solution till pH became 12. Then to this was added hydrochloric acid and the pH was readjusted to 7.4. The mixture was extracted with four 100 ml portions of chloroform. The extract was dried over anhydrous sodium sulfate. The solvent was removed under reduced pressure. A residue was recrystallized from a mixture of chloroform and ethanol twice to yield 133 mg of the titled compound.

Melting point: 244°–245° C. $[\alpha]_D^{25}$: −343.48° (c=0.545, 1N NaOH) $^1$H-NMR (400 MHz, 0.1N NaOD) δ ppm: 1.21–1.83 (6H, m), 2.39–2.65 (5H, m), 2.92–3.00 (1H, m), 3.18–3.42 (3H, m), 3.88–4.15 (3H, m), 4.95–5.15 (1H, m), 7.68 (1H, d, J=14.6Hz), 8.44 (1H, s). Elementary analysis, for $C_{21}H_{23}F_2N_3O_3$: Calcd. (%): C 62.52; H 5.75; N 10.42 Found (%): C 62.50; H 5.59; N 10.24

EXAMPLE 5

7-[(S,S)-2,8-diazabicyclo[4.3.0]nonan-8-yl]-6,8-difluoro-1-[(1R,2S)-2-fluorocyclopropyl]-1,4-dihydro-4-oxoquinoline-3-carboxylic acid

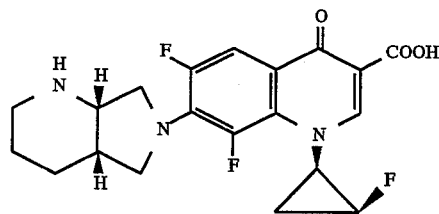

A solution of 301 mg of 6,7,8-trifluoro-1-[(1R,2S)-2-fluorocyclopropyl]-1,4-dihydro-4-oxoquinoline-3-carboxylic acid (JP-A-5-163244), 463 mg of (S,S)-2,8-diazabicyclo[4.3.0]nonane, 1 ml of triethylamine in 10 ml of acetonitrile was heated under reflux for 15 hours. To the mixture was added 50 ml of water, and the solvent was removed under reduced pressure. The mixture was extracted from three 50 ml portions of chloroform, and the extract was dried over anhydrous sodium sulfate. The solvent was removed under reduced pressure. A residue was dissolved in 10 ml of trifluoroacetic acid, and the solution was stirred at room temperature for 2 hours. Trifluoracetic acid was removed under reduced pressure and to a residue was added 1N sodium hydroxide aqueous solution till a pH became 12. To the solution was added hydrochloric acid till the pH became 7.4. The solution was extracted with six 50 ml portions of chloroform. The extract was dried over anhydrous sodium sulfate. The solvent was removed under reduced pressure and a residue was recrystallized from ethanol to yield 320 mg of the titled compound.

Melting point: 271°–273° C. $[\alpha]_D^{25}$: −130.90° (c=0.99, 1N NaOH) $^1$H-NMR (400 MHz, 0.1N NaOD) δ ppm: 1.45–1.80 (6H, m), 2.29–2.39 (1H, m), 2.55–2.65 (1H, m), 2.88–2.95 (1H, m), 3.31–3.38 (1H, m), 3.43–3.60 (2H, m), 3.90–4.04 (3H, m), 4.92–5.14 (1H, m), 7.64 (1H, d, J=14.7Hz), 8.39 (1H, s). Elementary analysis, for $C_{20}H_{20}F_3N_3O_3$; Calcd. (%): C 58.97; H 4.95; N 10.31 Found (%): C 58.72; H 4.91; N 10.22

REFERENCE EXAMPLE 14 trans-1-tert-Butoxycarbonyl-4-hydroxy-3-[(1R]-1-phenylethylamino]pyrrolidine (7)

A solution of 29.7 g of 1-tert-butoxycarbonyl-3,4-epoxypyrrolidine and 41 ml of (R)-(+)-α-methylbenzylamine in 250 ml of ethanol was heated under reflux for 16 hours. The solvent was removed under reduced pressure, and a residue was subjected to silica gel column chromatography. From an eluant of a mixture of chloroform and methanol (98:2 by volume.), an oily titled compound weighing 15.3 g was obtained.

¹H-NMR (400 MHz, CDCl₃) δ ppm: 1.30–1.50 (12H, m), 2.84–4.10 (7H, m), 7.22–7.35 (5H, m).

REFERENCE EXAMPLE 15 trans-1-tert-Butoxycarbonyl-4-hydroxy-3-[(1R)-1-phenylethyl-amino]pyrrolidine 8a, 8b To a solution of 7.56 g of trans-1-tert-butoxycarbonyl-4-hydroxy-3-[(1R)-1-phenylethylamino]pyrrolidine in 50 ml of dichloromethane was added 2.4 ml of chloroacetyl chloride at −20° C. and the mixture was stirred at that temperature for 2 hours. To the mixture was added 50 ml water, and an organic layer was separated. The organic layer was washed with 1N hydrochloric acid (50 ml, once) saturated sodium chloride aqueous solution (50 ml, once). The organic layer was dried over anhydrous sodium sulfate and the solvent was removed under a reduced pressure. A residue was subjected to silica gel column chromatography. From a fraction of a mixture of hexane and ethyl acetate (4:1 by volume) 3.14 g of the lower polar diastereomer of the titled compound was obtained. And further, from a fraction of a mixture of hexane and ethyl acetate (1:1), 3.85 g of the other higher polar diastereomer (8b) of the titled compound was obtained.

Diastereomer 8a:
¹H-NMR (400 MHz, CDCl₃) δ ppm: 1.43 (9H, s), 1.68 (3H, d, J=6.8Hz), 3.10–3.87 (5H, m), 4.20 and 4.25 (each 1H, each d, J=12.7Hz), 4.64 (1H, brs), 5.17 (1H, brs).

Diastereomer 8b:
¹H-NMR (400 MHz, CDCl₃) δ ppm: 1.37 (9H, s), 1.75 (3H, d, J=6.8Hz), 2.80–2.90 (1H, m), 3.05–3.13 (1H, m), 3.26–3.35 (1H, m), 3.40–3.49 (1H, m), 3.79–3.84 (1H, m), 4.23 (2H, s), 4.89–4.95 (1H, m), 5.12–5.19 (1H, m).

REFERENCE EXAMPLE 16 trans-8-tert-Butoxycarbonyl-5-[(1R)-1-phenylethyl]-4-oxo-2-oxa-5,8-diazabicyclo[4.3.0]nonane 9a To a solution of 3.14 g of trans-1-tert-butoxycarbonyl-4-hydroxy-3-[(1R)-1-phenylethylamino]pyrrolidine 8a in 200 of tetrahydrofuran was added 1 g of potassium tert-butoxide. The mixture was stirred at room temperature for 20 minutes. The solvent was removed under reduced pressure and a residue was subjected to silica gel column chromatography. From an eluant of a mixture of hexane and ethyl acetate (1:1 by volume), the titled compound 9a weighing 2.45 g was obtained as an oil.

¹H-NMR (400 MHz, CDCl₃) δ ppm: 1.41 (9H, s), 1.56–1.62 (3H, m), 2.95–3.73 (5H, m), 3.97–4.05 (1H, m), 4.43, 4.49 (each 1H, each d, J=16.6Hz), 5.85–6.01 (1H, m), 7.30–7.43 (5H, m).

REFERENCE EXAMPLE 17 trans-8-tert-Butoxycarbonyl-5-[(1R)-1-phenylethyl]-4-oxo-2-oxa-5,8-diazabicyclo-[4.3.0]nonane 9b To a solution of 3.85 g of trans-1-tert-butoxycarbonyl-4-hydroxy-3-[(1R)-1-phenylethylamino]pyrrolidine 8b in 200 ml of tetrahydrofuran was added 1.23 g of potassium tert-butoxide. According to the same procedure as disclosed in the Reference Example 16, the titled compound 9b weighing 2.31 g was obtained as an oil.

¹H-NMR (400 MHz, CDCl₃) δ ppm: 1.34, 1.40 (9H, s), 1.66 (3H, d, J=7.3Hz), 2.10–2.29 (1H, m), 3.05–4.00 (5H, m), 4.48 (2H, s), 6.02 (1H, q, J=7.3Hz), 7.25–7.33 (5H, m).

REFERENCE EXAMPLE 18 trans-8-tert-Butoxycarbonyl-5-[(1R)-1-phenylethyl]-2-oxa-5,8-diazabicyclo[4.3.0]nonane 10a To a solution of 2.45 g of trans-8-tert-butoxycarbonyl -5-[(1R)-1-phenylethyl]-4-oxo-2-oxa-5,8-diazabicyclo[4.3.0]nonane 9a in 50 ml of tetrahydrofuran, was added 7.1 ml of diborane tetrahydrofuran complex 1M solution dropwise at 0° C. The mixture was stirred at room temperature for 14 hours. Then, 12 ml of diborane tetrahydrofuran complex was added to the solution, and the mixture was stirred at room temperature for 24 hours. To an ice-cooled mixture, was added 10 ml of water and, then, 20 ml of saturated sodium bicarbonate aqueous solution at room temperature. The mixture was stirred at room temperature for 1 hour. The mixture was extracted from 100 ml of ethyl acetate. The organic layer was separated and washed with two 100 ml portions of saturated sodium chloride aqueous solution and dried over anhydrous sodium sulfate. The solvent was removed under reduced pressure and a residue was subjected to silica gel column chromatography. From an eluant of a mixture of hexane and ethyl acetate (2:1), the titled compound 10a weighing 1.85 g was obtained as an oil.

¹H-NMR (400 MHz, CDCl₃) δ ppm: 1.31–1.45 (12H, m), 2.37–3.95 (11H, m), 7.20–7.45 (5H, m).

REFERENCE EXAMPLE 19 trans-8-tert-Butoxycarbonyl-5-[(1R)-1-phenylethyl]-2-oxa-5,8-diazabicyclo[4.3.0]nonane 10b Starting from 2.31 g of trans-8-tert-butoxycarbonyl -5-[(1R)-1-phenylethyl]-4-oxo-2-oxa-5,8-diazabicyclo[4.3.0]nonane 9b, the titled compound 10b weighing 1.88 g was obtained as an oil by the same procedure as disclosed in the Reference Example 18.

¹H-NMR (400 MHz, CDCl₃) δ ppm: 1.41–1.47 (12H, m), 2.15–2.25 (2H, m), 2.73–2.83 (1H, m), 2.96–3.05 (2H, m), 3.50–3.95 (6H, m), 7.20–7.38 (5H, m).

REFERENCE EXAMPLE 20 trans-2-Oxa-5,8-diazabicyclo[4.3.0]nonane ditrifluoroacetate 11a

A mixture of 1.85 g of trans-8-tert-butoxycarbonyl-5-[(1R)-1-phenylethyl]-2-oxa-5,8-diazabicyclo[4.3.0]nonane 10a and 500 mg of palladium on charcoal in 100 ml of ethanol was shaken under a pressured hydrogen atmosphere of 4 kg/cm² for 6 hours. Throughout the reaction, the reaction vessel was heated by irradiation with a tungsten lamp. The catalyst was removed by filtration, and the solvent of the filtrate was removed under reduced pressure. The residue was dissolved in 13 ml of trifluoroacetic acid, and to this was added 13 ml of trifluoroacetic acid at 0° C. The mixture was stirred at room temperature for 18 hours. The solvent was removed under reduced pressure, and to a residue was added diisopropyl ether. A resulting crystal was collected and dried to yield 1.64 g of the titled compound.

¹H-NMR (400 MHz, D₂O) δ ppm: 3.16–3.42 (3H, m), 3.53–3.64 (2H, m), 3.72–3.79 (2H, m), 3.83–4.02 (1H, m), 4.10–4.17 (1H, m), 4.27–4.32 (1H, m).

REFERENCE EXAMPLE 21 trans-2-Oxa-5,8-diazabicyclo[4.3.0]nonane ditrifluoroacetate 11b

Starting from 1.88 g of trans-8-tert-butoxycarbonyl-5-[(1R)-1-phenylethyl]-2-oxa-5,8-diazabicyclo[4.3.0]nonane 10b, the titled compound 11b weighing 1.69 g was obtained by the same procedure as disclosed in the Reference Example 20.

The ¹H-NMR spectra was identical to that of the other enantiomer 11a.

EXAMPLE 6

8-Chloro-7-[3,7-diazabicyclo[3.3.0]oct-1(5)-ene-3-yl]-6-fluoro-1-[(1R,2S)-2-fluorocyclopropyl]-1,4-dihydro-4-oxoquinoline-3-carboxylic acid

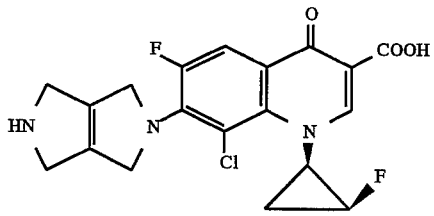

A solution of 318 mg of 8-chloro-6,7-difluoro-1-[(1R,2S)-2-fluorocyclopropyl]-1,4-dihydro-4-oxoquinoline-3-carboxylic acid, 544 mg of 3,7-diazabicyclo[3.3.0]oct-1(5)-ene dihydrobromide (JP-A-3-193779) and 2 ml of DBU in 20 ml of acetonitrile was heated under reflux for 15 hours. To the mixture was added 1N sodium hydroxide, and an insoluble material was removed by filtration. To the filtrate, was added hydrochloric acid till pH became 7.4, and the mixture was extracted by five 50 ml portions of chloroform. A combined organic layer was dried over anhydrous sodium sulfate and the solvent was removed under reduced pressure. The residue was recrystallized from a mixture of ethanol and ammonia water to yield 43.7 mg of the titled compound.

Melting point: 221°–223° C. $[\alpha]_D^{25}$: –66. (c=0.19, 1N NaOH) $^1$H-NMR (400 MHz, 0.1N NaOD) δ ppm: 1.37–1.4 (1H, m), 1.62–1.73 (1H, m), 3.68 (4H, s), 4.14–4.20, 4.25–4.37 (5H, each m), 4.95–4.99 and 5.11–5.14 (1H, m), 7.95 (1H, d, J=12.7Hz), 8.54 (1H, s). Elementary analysis, for $C_{19}H_{16}ClF_2N_3O_3 \cdot H_2O$; Calcd. (%): C 53.59; H 4.26; N 9.87 Found (%): C 53.60; H 4.06; N 9.76

EXAMPLE 7

(+)-8-Chloro-6-fluoro-1-[(1R,2S)-2-fluorocyclopropyl]-7-[trans-2-oxa-5,8-diazabicyclo[4.3.0]-nonan-8-yl]-1,4-dihydro-4-oxoquinoline-3-carboxylic acid

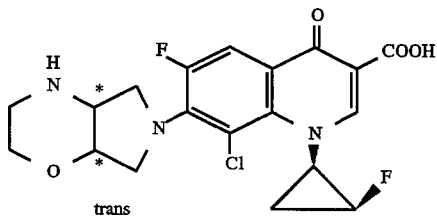

A solution of 159 mg of 8-chloro-6,7-difluoro-1-[(1R,2S)-2-fluorocyclopropyl]-1,4-dihydro-4-oxoquinoline-3-carboxylic acid, 356 mg of trans-2-oxa-5,8-diazabicyclo[4.3.0]nonane ditrifluoroacetate 11a and 1 ml of triethylamine in 5 ml of acetonitrile was heated under reflux for 6 hours. The solvent was removed under reduced pressure, and to a residue was added 1N sodium hydroxide till pH became 12. The pH of the mixture was readjusted to 7.4 by adding hydrochloric acid. A resulting crystalline was collected by filtration and washed by ethanol. Then the crystalline was recrystallized from a mixture of ethanol and chloroform to yield 40.5 mg of the titled compound.

Melting point: 141°–145° C. $[\alpha]_D^{25}$: 179.38 (c=0.485, 1N NaOH) $^1$H-NMR (400 MHz, 0.1N NaOD) δ ppm: 1.44–1.75 (2H, m), 3.00–3.17 (3H, m), 3.55–3.85 (6H, m), 4.06–4.12 (1H, m), 4.29–4.35 (1H, m), 4.95–5.09 (1H, m), 7.84 (1H, d, J=13.2Hz), 8.54 (1H, s). Elementary analysis, for $C_{19}H_{18}ClF_2N_3O_4$; Calcd. (%): C 53.59; H 4.26; N 9.87 Found (%): C 53.33; H 4.54; N 9.63

EXAMPLE 8

(–)-8-Chloro-6-fluoro-1-[(1R,2S)-2-fluorocyclopropyl]-7-[trans-2-oxa-5,8-diazabicyclo[4.3.0]nonan-8-yl]-1,4-dihydro-4-oxoquinoline-3-carboxylic acid

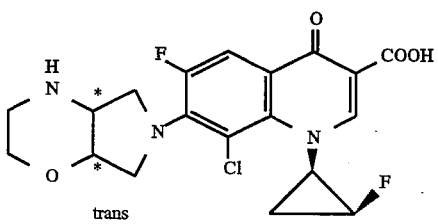

A solution of 159 mg of 8-chloro-6,7-difluoro-1-[(1R,2S)-2-fluorocyclopropyl]-1,4-dihydro-4-oxoquinoline-3-carboxylic acid, 356 mg of trans-2-oxa-5,8-diazabicyclo[4.3.0]nonane ditrifluoroacetate 11b and 1 ml of triethylamine in 5 ml of acetonitrile was heated under reflux for 6 hours. The solvent was removed under reduced pressure, and a resulting crystal was washed successively by acetonitrile, water and ethanol. The crystal was recrystallized from a mixture of ethanol, chloroform and ammonia water to yield 40.5 mg of the titled compound.

Melting point: 267°–270° C. (decomp.) $[\alpha]_D^{25}$: –295.38° (c=0.715, 1N NaOH) $^1$H-NMR (400 MHz, 0.1N NaOD) δ ppm: 1.21–1.35, 1.53–1.66 (each 1H, each m), 3.00–3.15 (3H, m), 3.45–3.55 (2H, m), 3.78–4.02 (4H, m), 4.07–4.13 (1H, m), 4.17–4.23 (1H, m), 4.97–5.15 (1H, m), 7.80 (1H, d, J=13.7Hz), 8.44 (1H, s). Elementary analysis, for $C_{19}H_{18}ClF_2N_3O_4 \cdot \frac{1}{4}H_2O$; Calcd. (%): C 53.03; H 4.33; N 9.76 Found (%): C 53.08; H 4.36; N 9.60

EXAMPLE 9

5-Amino-6,8-difluoro-1-[(1R,2S)-2-fluorocyclopropyl]-7-(trans-2-oxa-5,8-diazabicyclo[4.3.0]nonan-8-yl)-1,4-dihydro-4-oxoquinoline-3-carboxylic acid

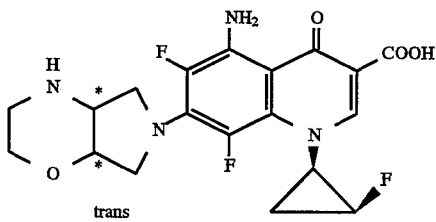

A solution of 158 mg of 5-amino-6,7,8-difluoro-1-[(1R,2S)-2-fluorocyclopropyl]-1,4-dihydro-4-oxoquinoline-3-carboxylic acid, 356 mg of trans-2-oxa-5,8-diazabicyclo[4.3.0]nonane ditrifluoroacetate 11b and 1 ml of triethylamine in 5 ml of acetonitrile was heated under reflux for 22 hours. The solvent was removed under reduced pressure and a crystal was collected and washed by acetonitrile, water and ethanol. The crystal was recrystallized from a mixture of ethanol and ammonia water to yield 147 mg of the titled compound.

Melting point: 292°–294° C. $[\alpha]_D^{25}$: −297.14° (c=0.595, 1N NaOH) $^1$H-NMR (400 MHz, 0.1N NaOD) δ ppm: 1.41–1.59 (2H, m), 2.82–2.97 (3H, m), 3.51–3.79 (7H, m), 4.01–4.04 (1H, m), 4.82–5.03 (1H, m), 8.18 (1H, s). Elementary analysis for $C_{19}H_{19}F_3N_4O_4$, Calcd. (%): C 53.77; H 4.51; N 13.30 Found (%): C 54.03; H 4.34; N 13.29

REFERENCE EXAMPLE 22

1-tert-Butoxycarbonyl-3-[N-chloroacetyl-N -(1R)-1-phenylethylamino]-4-oxopyrrolidine 12a To a solution of 1.13 g of pyridinium chloro chromate in 5 ml of dichloromethane was added a solution of trans-1-tert-butoxycarbonyl-3-[N-chloroacetyl-(1R)-phenylethylamino]-4-hydroxypyrrolidine 8a in 10 ml of dichloromethane and the mixture was stirred for 2 hours. To the mixture was added 0.565 g of pyridinium chloro chromate, and the mixture was stirred overnight. A supernatant of the mixture was subjected to silica gel column chromatography. From an eluant of a mixture of hexane and ethyl acetate (1:1 by volume), the titled compound 12a weighing 995 mg was obtained.

$^1$H-NMR (CDCl$_3$) δ ppm: 1.42 (9H, 2s), 1.67–1.75 (3H, m), 3.31–4.26 (8H, m), 5.17–5.24 (1H, m), 7.31–7.53 (5H, m).

REFERENCE EXAMPLE 23

1-tert-Butoxycarbonyl-3-[N-chloroacetyl-N -(1R)-1-phenylethylamino]-4-oxopyrrolidine 12b To a solution of 19.77 g of pyridinium chloro chromate in 50 ml of dichloromethane was added a solution of trans-1-tert-butoxycarbonyl-3-[N-chloroacetyl-(1R)-pnenylethylamino]-4-hydroxypyrrolidine 8b in 100 ml of dichloromethane and the mixture was stirred for over-night. A supernatant of the mixture was subjected to silica gel column chromatography. From an eluant of a mixture of hexane and ethyl acetate (1:1 by volume), the titled compound 12b weighing 9.25 g was obtained.

$^1$H-NMR (CDCl$_3$) δ ppm: 1.39 (9H, s), 1.74 (3H, d, J=10.25Hz), 3.31–3.43 (3H, m), 3.73–3.97 (2H, m), 4.21 (2H, 2d, J=12.21Hz), 5.23 (1H, dd, J=6.84, 13.67Hz), 7.29–7.41 (5H, m).

REFERENCE EXAMPLE 24 cis-8-tert-Butoxycarbonyl-5-[(1R)-1-phenylethylamino]-4-oxo-2-oxa-5,8-diazabicyclo [4.3.0]nonane 13a To a solution of 5 g of 1-tert-butoxycarbonyl-3-[N-chloroacetyl-N-(1R)-1-phenylethylamino]-4-oxopyrrolidine 12a in 100 ml of isopropyl alcohol was slowly added 198 mg of sodium borohydride, and the mixture was stirred at room temperature for 30 minutes. The solvent was removed under reduced pressure, and a residue was extracted by chloroform. The extract was washed by 10% citric acid aqueous solution and dried over anhydrous sodium sulfate. A residue was subjected to silica gel column chromatography. From an eluant of a mixture of hexane and ethyl acetate (3:1 by volume), the titled compound 13a weighing 560 mg was obtained.

$^1$H-NMR (CDCl$_3$) δ ppm: 1.43 (9H, s), 1.53 (3H, d, J=7.32Hz), 3.20–3.48 (4H, m), 3.72–3.91 (1H, m), 3.99–4.00 (1H, m), 4.30 (1H, dd, J=6.61, 63.96Hz), 6.10 (1H, dd, J=7.32, 14.65Hz), 7.31–7.39 (5H, m).

REFERENCE EXAMPLE 25 cis-8-tert-Butoxycarbonyl-5-[(1R)-1-phenylethylamino]-2-oxa-5,8-diazabicyclo[4.3.0] nonane 14a To a solution of 191 mg of cis-8-tert-butoxycarbonyl-5-[(1R)-1-phenylethylamino]-4-oxo-2-oxa-5,8-diazabicyclo [4.3.0]nonane 13a in 6 ml of tetrahydrofuran was added 1 ml of 1M diborane tetrahydrofuran complex dropwise. The mixture was stirred at 5° C. for 3 days. To an ice-cooled reaction mixture was added 15 ml of water and 10 ml of saturated potassium carbonate aqueous solution, and the mixture was stirred. The mixture was extracted by chloroform and the organic layer was separated. The organic layer was washed by saturated sodium chloride aqueous solution. The organic layer was dried over anhydrous sodium sulfate. The solvent was removed under reduced pressure and a residue was subjected to silica gel column chromatography. From an eluant of a mixture of hexane and ethyl acetate (3:1 by volume), the titled compound 14a weighing 103 mg was obtained.

$^1$H-NMR (400 MHz, CDCl$_3$) δ ppm: 1.46–1.58 (12H, m), 2.23–2.26 (1H, m), 2.49 (1H, brs), 3.31–3.74 (8H, m), 4.05 (1H, brs), 7.30 (5H, brs).

REFERENCE EXAMPLE 26 cis-8-tert-Butoxycarbonyl-2-oxa -5,8-diazabicyclo [4.3.0]nonane 15a

A mixture of 417 mg of cis-8-tert-butoxycarbonyl-5-[(1R) -1-phenylethylamino]-2-oxa-5,8-diazabicyclo[4.3.0]nonane 14a and 200 mg of 10% palladium on charcoal in 50 ml of ethanol was shaken under a pressured hydrogen atmosphere of 4.5 kg/cm$^2$ for 4 hours. Then further 100 mg of 10% palladium on charcoal was added and hydrogenation was carried out under the above-mentioned condition. Throughout the reaction, the reaction vessel was heated by irradiation with a tungsten lamp. The catalyst was removed by filtration, and the solvent of the filtrate was removed under reduced pressure. The residue was subjected to silica gel column chromatography. From an eluant of chloroform containing 10% methanol, the titled compound 15a weighing 286 mg was obtained.

$^1$H-NMR (CDCl$_3$) δ ppm: 1.45 (9H, s), 2.41 (1H, brs), 2.71–2.72 (1H, m), 3.10–3.16 (1H, m), 3.39–3.61 (6H, m), 3.83–3.86 (1H, m), 3.98–3.99 (1H, m).

REFERENCE EXAMPLE 27 cis-2-Oxa-5,8-diazabicyclo[4.3.0]nonane ditrifluoroacetate 16a

To a solution of 268 mg of cis-8-tert-butoxycarbonyl-2-oxa-5,8-diazabicyclo[4.3.0]nonane 15a in 4 ml of dichloromethane was added 3 ml of trifluoroacetic acid under ice-cooling with stirring. The solution was stirred at the same temperature for 30 minutes. The solvent was removed under reduced pressure, and to a residue was added diisopropyl ether. A resulting solid was washed by diisopropyl ether and dried to yield 366 mg of the titled compound.

$^1$H-NMR (D$_2$O) δ ppm: 3.11–3.49 (4H, m), 3.57–3.77 (3H, m), 3.99 (1H, dd, J=3.42, 13.19Hz), 4.07 (1H, td, J=9.76Hz), 4.40 (1H, t, J=3.42Hz).

REFERENCE EXAMPLE 28 cis-8-tert-Butoxycarbonyl-5-[(1R)-1-phenylethylamino]-4-oxo-2-oxa-5,8-diazabicyclo [4.3.0]nonane 13b To a solution of 3.2 g of 1-tert-butoxycarbonyl-3-[N -chloroacetyl-N-(1R)-1-phenylethylamino]-4-oxopyrrolidine 12b in 60 ml of methanol was added 127 mg of sodium borohydride by a small portion, and the mixture was stirred at room temperature for 30 minutes. The solvent

29 was removed under reduced pressure, and a residue was extracted by chloroform. The extract was washed by 10% citric acid aqueous solution and dried over anhydrous sodium sulfate. A residue was dissolved in 15 ml of tetrahydrofuran, and to this was added 442 mg of potassium tert-butoxide and the mixture was stirred for 20 minutes. To the mixture was added 10% citric acid aqueous solution, and the mixture was stirred. The mixture was extracted by chloroform. The extract was dried over anhydrous sodium sulfate, and the solvent was removed under reduced pressure to yield 2.79 g of the crude product of the titled compound.

REFERENCE EXAMPLE 29 cis-8-tert-Butoxycarbonyl-5-[(1R)-1-phenylethylamino]-2-oxa-5,8-diazabicyclo[4.3.0]nonane 14b To a solution of 3.32 g of cis-8-tert-butoxycarbonyl-5-[(1R)-1-phenylethylamino]-4-oxo-2-oxa-5,8-diazabicyclo[4.3.0]nonane 13b in 6 ml of tetrahydrofuran was added 19.2 ml of 1M diborane tetrahydrofuran complex dropwise under ice-cooling. The mixture was stirred at room temperature overnight. To the mixture was added 5 ml of the diborane solution mentioned above and the mixture was stirred at room temperature for 2 hours. To an ice-cooled reaction mixture was added water and saturated potassium carbonate aqueous solution. The mixture was extracted by ethyl acetate. The organic layer was washed by saturated sodium chloride aqueous solution. The organic layer was dried over anhydrous sodium sulfate and the solvent was removed under reduced pressure. A residue was subjected to silica gel column chromatography. From an eluant of a mixture of hexane and ethyl acetate (3:1 by volume), the titled compound 14b weighing 2.17 g was obtained.

$^1$H-NMR (CDCl$_3$) δ ppm: 1.27–1.30 (3H, m), 1.39–1.48 (10H, m), 2.68–2.73 (1H, m), 2.79–2.82 (1H, m), 3.02–3.71 (6H, m), 3.84–3.86 (1H, m), 3.90–3.93 (1H, m), 7.23–7.37 (5H, m).

REFERENCE EXAMPLE 30 cis-2-Oxa-5,8-diazabicyclo[4.3.0]nonane ditrifluoroacetate 16b

A mixture of 2.46 g of cis-8-tert-butoxycarbonyl-5-[(1R)-1-phenylethylamino]-2-oxa-5,8-diazabicyclo[4.3.0]nonane 14b and 1 g of 10% palladium on charcoal in 50 ml of ethanol was shaken under a pressured hydrogen atmosphere of 4.5 kg/cm$^2$ for 4 hours. Throughout the reaction, the reaction vessel was heated by irradiation with a tungsten lamp. The catalyst was removed by filtration, and the solvent of the filtrate was removed under reduced pressure. To a residue was added 40 ml of dichloromethane, and to this was added 20 ml of trifluoroacetic acid under ice-cooling with stirring. The solution was stirred at the same temperature for 2 hours. The solvent was removed under reduced pressure, and to a residue was added diisopropyl ether. A resulting solid was washed by diisopropyl ether and dried to yield 2.17 g of the titled compound.

$^1$H-NMR D$_2$O) δ ppm: 3.14–3.50 (3H, m), 3.57–3.79 (3H, m), 3.99 (1H, dd, J=3.42, 13.19Hz), 4.08 (1H, td, J=9.76Hz), 4.40 (1H, t, J=2.93Hz).

30

EXAMPLE 10

(−)-5-Amino-7-[cis-2-azabicyclo[4.3.0]nonan-8-yl]-6,8-difluoro-1-[(1R,2S)-2-fluorocyclopropyl]-1,4-dihydro-4-oxoquinoline-3-carboxylic acid

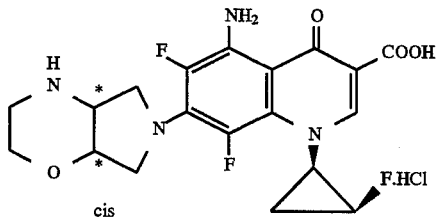

A solution of 300 mg of 5-amino-6,7,8-difluoro-1-[(1R,2S)-2-fluorocyclopropyl]-1,4-dihydro-4-oxoquinoline-3-carboxylic acid, 534 mg of cis-2-oxa-5,8-diazabicyclo[4.3.0]nonane ditrifluoroacetate 16b, 1.4 ml of triethylamine in 15 ml of acetonitrile was heated under reflux for 7.5 hours. The solvent was removed under reduced pressure and a resulting crystal was collected and recrystallized from a mixture of ethanol and chloroform to yield 221 mg of the titled compound.

Melting point: 228°–231° C. [α]$_D$: −133.33° (c=0.708, 1N NaOH) $^1$H-NMR (1N NaOD) δ ppm: 1.52–1.71 (2H, m), 2.78 (1H, d, J=3.67Hz), 3.12–3.19 (1H, m), 3.57–3.69 (3H, m), 3.73 (1H, dd, J=2.44, 11.72Hz), 3.82–3.87 (1H, m), 3.95 (1H, d, J=11.72Hz), 4.06–4.11 (2H, m), 4.19 (1H, s), 4.96–5.14 (1H, m), 8.25 (1H, d, J=1.47Hz).

EXAMPLE 11

8-Chloro-6-fluoro-1-[(1R,2S)-2-fluorocyclopropyl]-7-(cis-2-oxa-5,8-diazabicyclo[4.3.0]nonan-8-yl)-1,4-dihydro-4-oxoquinoline-3-carboxylic acid

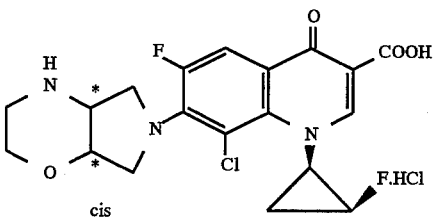

A solution of 213 mg of 8-chloro-6,7-difluoro-1-[(1R,2S)-2-fluorocyclopropyl]-1,4-dihydro-4-oxoquinoline-3-carboxylic acid, 356 mg of cis-2-oxa-5,8-diazabicyclo[4.3.0]nonane ditrifluoroacetate 16b and 1 ml of triethylamine in 10 ml of acetonitrile was heated under reflux for 8 hours. The solvent was removed under reduced pressure, and to a residue was added 1N sodium hydroxide. The mixture was washed by chloroform, and the aqueous layer was neutralized by adding hydrochloric acid. The mixture was extracted by chloroform. The organic layer was dried over anhydrous sodium sulfate. The solvent was removed under reduced pressure and to a residue was added 460 μl of concd. hydrochloric acid and 6.5 ml of 1N hydrochloric acid. A resulting crystal was collected to yield 6 mg of the titled compound.

Melting point: 191°–196° C. $^1$H-NMR (1N NaOD) δ ppm: 0.73–0.75 (1H, m), 0.88–0.93 (1H, m), 1.02–1.10 (1H, m), 1.17–1.25 (1H, m), 2.67 (1H, d, J=13.6Hz), 3.05–3.12 (1H, m), 3.32–3.37 (2H, m), 3.57–3.64 (2H, m), 3.85 (1H, d, J=11.7Hz), 4.09–4.23 (4H, m), 7.71 (1H, d, J=13.6Hz), 8.40 (1H, s). Elementary analysis for $C_{19}H_{19}Cl_2F_2N_3O_4 \cdot 3/2H_2O$ Calcd. (%): C 46.64; H 4.53; N 8.59 Found (%): C 46.56; H 4.26; N 8.48

EXAMPLE 12

The partition coefficient in a solvent system of chloroform and phosphate buffer (pH 7.4) of the compounds of the present invention and relating compounds was determined according to the method reported in *Journal of Medicinal Chemistry*, 1993, 36, 3444–3448, and the results are summarized as follows.

| Compound (Ex. No.) | Partition Coefficient |
|---|---|
| Ex. 2 | p' = 6.69 |
| Ex. 4 | p' = 3.73 |
| Ex. 5 | p' = 5.84 |
| Bay y 3118 | p' = 35.8 |
| Ex. 7 | p' = 26.9 |
| Ex. 8 | p' = 24.8 |
| Compound A* | p' = 112 |

*8-chloro-1-cyclopropyl-6-fluoro-1,4-dihydro-7-(trans-2-oxa-5,8-diazabicyclo[4.3.0]nonan-8-yl)-4-oxo-3-quinoline-3-carboxylic acid (racemic, JP-A-5-271229)

TABLE 1

| | MIC data (µg/ml) | | | | | |
|---|---|---|---|---|---|---|
| | Compound (Example No.) | | | | | |
| Bacteria | Ex. 2 | Ex. 3 | Ex. 4 | Ex. 5 | Ex. 6 | Ex. 9 |
| *E. coli* NIHJ | ≦0.003 | 0.006 | 0.013 | 0.013 | 0.025 | 0.006 |
| *S. flexneli*, 2A, 5503 | 0.006 | 0.013 | 0.025 | 0.013 | 0.013 | 0.013 |
| *Pr. vulgaris*, 08601 | 0.013 | 0.025 | 0.025 | 0.013 | 0.013 | 0.025 |
| *Pr. mirabiris*, IFO-3849 | 0.025 | 0.05 | 0.05 | 0.05 | 0.05 | 0.05 |
| *Ser. marcescens*, 10100 | 0.025 | 0.05 | 0.05 | 0.05 | 0.20 | 0.10 |
| *Ps. aeruginosa*, 32104 | 0.05 | 0.05 | 0.10 | 0.10 | 0.20 | 0.20 |
| *Ps. aeruginosa*, 32121 | 0.05 | 0.05 | 0.05 | 0.05 | 0.10 | 0.05 |
| *S. aureus*, 209P | 0.013 | 0.025 | 0.025 | 0.025 | 0.025 | 0.013 |
| *S. aureus*, Smith | 0.006 | 0.006 | 0.013 | 0.013 | 0.013 | 0.006 |
| *S. epidermidis*, 56500 | 0.05 | 0.025 | 0.05 | 0.10 | 0.10 | 0.025 |
| *Str. pyogenes*, G-36 | 0.05 | 0.10 | 0.10 | 0.10 | 0.10 | 0.20 |
| *Str. faecalis*, ATCC 19433 | 0.10 | 0.10 | 0.20 | 0.20 | 0.39 | 0.10 |

While the invention has been described in detail and with reference to specific examples thereof, it will be apparent to one skilled in the art that various changes and modifications can be made therein without departing from the spirit and scope thereof.

What is claimed is:

1. A compound represented by formula (I):

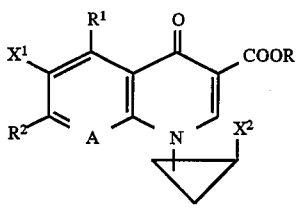

(I)

wherein $X^1$ and $X^2$ which may be the same or different, each represents a halogen atom;

$R^1$ represents a hydrogen atom, a hydroxyl group, an alkyl group having from 1 to 6 carbon atoms, or an amino group;

$R^2$ represents a bicyclic heterocyclic substituent represented by formula:

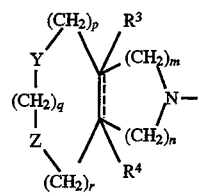

wherein $R^3$ and $R^4$ each represents a hydrogen atom;

Y represents a group of formula:

wherein $R^7$ represents a hydrogen atom;

Z represents a group of formula:

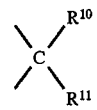

wherein $R^{10}$ and $R^{11}$ each represents a hydrogen atom;

m and n each represent an integer of 1;

p represents 0;

q represents 0, 1 or 2;

r represents 0 or 1; and the sum of q and r is an integer of 2;

said bicyclic heterocyclic substituent may be substituted with 1 to 4 alkyl groups each having from 1 to 6 carbon atoms;

A represents a group of formula:

wherein $X^3$ represents a hydrogen atom, a halogen atom, an alkyl group having from 1 to 6 carbon atoms or an alkoxy group having from 1 to 6 carbon atoms; and R represents a hydrogen atom, or a salt thereof.

2. A compound as claimed in claim 1, wherein $R_2$ is a bicyclic heterocyclic substituent having a single stereoisomerism, or a salt thereof.

3. A compound as claimed in claim 1, wherein the 1,2-cis-halogenocyclopropyl group is a substituent having a single stereoisomerism, or a salt thereof.

4. A compound as claimed in claim 1, wherein the 1,2-cis-halogenocyclopropyl group is a (1R,2S)-2-halogenocyclopropyl group, or a salt thereof.

5. A compound as claimed in claim 4, wherein $X^2$ is a fluorine atom, or a salt thereof.

6. A compound as claimed in claim 1, 2, 3, 4, or 5, wherein $R^2$ is a 2,8-diazabicyclo[4.3.0]nonan-8-yl group, or a salt thereof.

7. A compound as claimed in claim 6, wherein $R^2$ is a (S,S)-2,8-diazabicyclo[4.3.0]nonan-8-yl group, or a salt thereof.

8. A compound of claim 1, wherein the compound consists of a single diastereomer, or a salt thereof.

9. 8-Chloro-7-(2,8-diazabicyclo[4.3.0]nonan -8-yl)-chloro-6-fluoro-1-[(1R,2S)-2-fluorocyclopropyl]-1,4-dihydro -4-oxoquinoline-3-carboxylic acid, or a salt thereof.

10. 5-Amino-7-[(S,S)-2,8-diazabicyclo[4.3.0]nonan-8-yl] -6,8-difluoro-1-[(1R,2S)-2-fluorocyclopropyl]-1,4-dihydro-4-oxoquinoline-3-carboxylic acid, or a salt thereof.

11. 7-[(S,S)-2,8-diazabicyclo[4.3.0]nonan-8-yl]-6-fluoro-1-[(1R,2S)-2-fluorocyclopropyl]-8-methyl-1,4-dihydro -4-oxoquinoline-3-carboxylic acid, or a salt thereof.

12. 7-[(S,S)-2,8-diazabicyclo[4.3.0]nonan-8-yl]-6,8-difluoro-1-[(1R,2S)-2-fluorocyclopropyl]-1,4-dihydro-4-oxoquinoline-3-carboxylic acid, or a salt thereof.

13. An antibacterial agent comprising a compound of claim 1 or a salt thereof, and a carrier.

14. A compound which is 8-chloro-7-(2,8-diazabicyclo [4.3.0]nonan-8-yl) -8-chloro-6-fluoro -1-[(1R,2S)-2-fluorocyclopropyl]-1,4-dihydro-4-oxoquinoline -3-carboxylic acid, 5-amino-7-[(S,S)-2,8-diazabicyclo [4.3.0]nonan -8-yl]-6,8-difluoro-1-[(1R,2S)-2-fluorocyclopropyl]-1,4-dihydro-4-oxoquinoline-3-carboxylic acid, 7-[(S,S)-2,8-diazabicyclo[4.3.0]nonan-8-yl]-6-fluoro-1-[(1R,2S) -2-fluorocyclopropyl]-8-methyl-1, 4-dihydro-4-oxoquinoline-3-carboxylic acid, 7-[(S,S)-2,8-diazabicyclo[4.3.0]nonan-8-yl]-6,8-difluoro -1-[(1R,2S)-2-fluorocyclopropyl]-1,4-dihydro-4-oxoquinoline-3-carboxylic acid, or a salt thereof.

* * * * *